US006210682B1

(12) United States Patent
Estes et al.

(10) Patent No.: US 6,210,682 B1
(45) Date of Patent: Apr. 3, 2001

(54) ROTAVIRUS ENTEROTOXIN NSP4 AND METHODS OF USING SAME

(75) Inventors: Mary K. Estes, Friendswod; Judith Ball, Conroe, both of TX (US); Peng Tien, West New York, NY (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 08/973,961

(22) PCT Filed: Jun. 14, 1996

(86) PCT No.: PCT/US96/10523

§ 371 Date: May 26, 1998

§ 102(e) Date: May 26, 1998

(87) PCT Pub. No.: WO97/00088

PCT Pub. Date: Jan. 3, 1997

Related U.S. Application Data

(63) Continuation-in-part of application No. 08/628,014, filed on Apr. 4, 1996, now abandoned.

(60) Provisional application No. 60/000,220, filed on Jun. 14, 1995.

(51) Int. Cl.$^7$ ............................ A61K 39/15; C07K 14/14

(52) U.S. Cl. .................................... 424/215.1; 424/139.1; 424/147.1; 424/159.1; 424/184.1; 424/185.1; 424/186.1; 435/69.1; 435/69.3; 435/235.1; 435/320.1; 530/300; 530/326; 530/324; 530/325; 536/23.72

(58) Field of Search ............................. 424/139.1, 147.1, 424/159.1, 184.1, 185.1, 186.1, 215.1; 435/69.1, 69.3, 235.1, 320.1; 530/300, 326, 324, 325; 536/23.72

(56) References Cited

U.S. PATENT DOCUMENTS

| | | |
|---|---|---|
| 4,341,763 | 7/1982 | Zygraich . |
| 4,344,935 | 8/1982 | Leclerc et al. . |
| 4,636,385 | 1/1987 | Plotkin et al. . |
| 4,686,281 | 8/1987 | Dodin et al. . |
| 4,704,275 | 11/1987 | Wyatt et al. . |
| 4,745,051 | 5/1988 | Smith . |
| 4,853,333 | 8/1989 | Hsiao et al. . |
| 4,861,864 | 8/1989 | Atkinson et al. . |
| 4,898,815 | 2/1990 | Dodin et al. . |
| 5,147,639 | 9/1992 | Welter . |
| 5,186,933 | 2/1993 | Estes . |
| 5,474,773 | 12/1995 | Ward . |

FOREIGN PATENT DOCUMENTS

| | | |
|---|---|---|
| 0251467 | 1/1988 | (EP) . |
| WO9201784 | 2/1992 | (WO) . |
| WO9401134 | 1/1994 | (WO) . |

OTHER PUBLICATIONS

Burnette, W.N., Parameters for the Rational Design of Genetic Toxoid Vaccines, Adv Exp Med Biol. 1996; 397:61–7.

Rappuoli, R. et al., Genetic Detoxification of Bacterial Toxins: A New Approach to Vaccine Development, In t. Arch. Allergy Immunol 1995; 108:327–333.

Estes, M., "Cloning and nucleotide sequence of the simian rotavirus gene 6 . . . ," *Nucleic Acids Research,* 12(4):1875–1887 (1984).

Miller, L., "Insect Baculoviruses: Powerful Gene Expression Vectors," *BioEssays,* 11:91–95 (Oct. 1989).

Estes, M., et al., "Antigenic structure of rotaviruses," *Immunochemistry of Viruses. The Basis for Serodiagnosis and Vaccines.,* 21:389–405 (1985).

Miller, L., "A Virus Vector for Genetic Engineering in Invertebrates." Genetic Engineering In The Plant Sciences, 14:203–224 (1981).

Estes, M., et al., *Immunobiology of Proteins and Peptides—III,* 201–214 (1985).

Kapikian, A., et al., "Rotaviruses," *Virology,* 37:863–906 (1985).

Mason, B., "Biochemical Mapping of the Simian Rotavirus SA11 Genome," *Journal of Virology,* 46:413–423 (May 1983).

Chan, W., et al., "Two Glycoproteins Are Produced from the Rotavirus Neutralization Gene," *Virology* 151:243–252 (1986).

Bican, P., et al. "Purification and Characterization of Bovine Rotavirus Cores," *Journal of Virology,* 43(3):1113–1117 (Sep. 1982).

Gorziglia, M., et al., "Biochemical Evidence for the Oligomeric (Possibly Trimeric) Structure . . . ," *J. Gen virol.,* 66:1889–1900 (1985).

Beards, G., et al., "Enzyme Linked Immunosobent Assays Based on Polyclonal . . . ," *Journal of Clinical Microbiology,* 19(2):248–254 (Feb. 1984).

Nakata, S., et al., "Antigenic Characterization and Elisa Detection of Adult Diarrhea Rotaviruses," *The Journal of Infectious Diseases,* 154:448–455 (Sep. 1996).

Estes, M., et al., "Simian rotavirus SA11 Replication in Cell Cultures," *Journal of Virology,* 31(3):810–815 (Sep. 1979).

Smith, G., et al., "Molecular Engineering of the *Autographa californica* nuclear Polyhedrosis Virus Genome . . . ," *Journal of Virology,* 46:584–593 (May 1983).

Both, G., et al., "Coding Assignment and Nucleotide Sequence of Simian Rotavirus SA11 Gene Segment," *Journal of Virology,* 48:335–339 (Nov. 1983).

Estes, Mary K., et al., *Journal of Virology,* 61(5):1488–1994 (May 1987).

(List continued on next page.)

*Primary Examiner*—Phuong T. Bui

(74) *Attorney, Agent, or Firm*—Fulbright & Jaworski L.L.P.

(57) ABSTRACT

Methods of immunization against rotavirus infection or rotavirus disease by administering to a subject a peptide NSP4 114–135, a peptide NSP4 120–147, or a toxoid thereof are disclosed.

6 Claims, 9 Drawing Sheets

OTHER PUBLICATIONS

Smith, Gale E., et al., "Modification and secretion of human interluken 2 produced . . . ," *Proc. Natl. Acad. Sci. USA,* 82:8404–8408 (Dec. 1985).

Miyamoto, Chikara, et al., "Production of Human c=myc Protein Insect Cells Infected with a Baculovirus Expression Vector," *Molecular and Cellular Biology,* 5(10):2860–2865 (Oct. 1985).

Hambraeus, B. Anna M., et al., "Animal model of rotavirus infection in rabbits protection obtained without shedding of viral antigen," *Arch Virol,* 107:237–251 (1989).

Summers, Max D., et al., *Genetically Altered Viruses & The Environment.* Cold Spring Harbor Laboratory 1985.

Brussow, Harald, et al., "Polypeptide Composition of Rotavirus Empty Capsids and Their Possible Use as a Subunit Vaccine," *J. Virol.,* 64:3635–3642 (1990).

Welch, Siao–Kun Wan, et al., "Rotavirus SA11 Genome Segment 11 Protein Is a Nonstructural Phosphoprotein," *J. Virol.,* 63:000–000 (1989).

Estes, Mary K., et al., "Synthesis and Characterization of Rotavirus Capsid Antigens Using a Baculovirus Expression System," Abstract U.S.—Japan Cooperative Medical Science Program, Bethesda, Maryland Oct. 28–Oct. 30 (1985).

Ward, C. W., "Structural Homologies between RNA Gene Segments 10 and 11 . . . ," *Virology,* 144(2):328–336 (1985).

Posses, R. D., "Cell–surface expression of influenza virus haemagglutinin in insect cells using a baculovirus vectors." *Virus Research,* 5:43–59 (1986).

Kuroda, K., et al., "Expression of the influenza virus haemagglutinin in insect cells by a baculovirus," *EMBD Jour.* 5(6):1359–1365 (1986).

Clark, et al., "Rotavirus Vaccines" *Vaccines,* Plotkin, et al. eds. W. B. Sounders Co., Philadelphia, 1988 p. 517–525.

Offit, et al., "Maternal Antibody—Mediated Protection Against Gastroenteritis Due . . . ," *J. Infect. Dis.* 152(6):1152–1158, (1985).

Daum et al., "New Developments in Vaccines," *Adv. Pediatr. Infect. Dis.* 6:1–57, (1991). (pp. 30–38 & 54–56 relevant to rotovirus enclosed).

Conner, et al., "Rotavirus Vaccines & Vaccination Potential" in *Current Topics in Microbiology and Immunology,* 185:286–326 (1994).

Both, G. W. et al., "Nucleotide sequence of the dsRNA segment 7 of Simian 11 rotavirus gene 8," *Nucleic Acids Research,* 12(3):1621–1625 (1984).

Both, G., et al., "A general strategy for cloning double–stranded BNA nucleotide sequence of the Simian–11 . . . ," *Nucleic Acids Research,* 10(22)7–75–7088 (1982).

Estes, et al., "Rotavirus Antigens," *Adv. Exp. Med. Biol.,* 185:201–214 (1984).

Bastardo, J. W., "Preparation and Characterization of Antisera to Electrophoretically Purified SA11 Virus Polypeptides," *Infectious Immunology,* 34(3):641–647 (1981).

Smith, G.E., et al., Production of Human Beta Interferon in Insect Cells Infected with a Baculovirus Expression Vector, *Mol. Cell. Biol.,* 3(12):2156–2165 (1983).

Ijaz, et al. "Effect of different routes of immunization . . ." *Antiviral Research,* 8(5–6):283–298 (1987).

Flores, J., et al., "Comparison of reactogenicity and antigenicity of M37 rotavirus vaccine and rhesus–rotavirus–based quadrivalent vaccine," *Lancet* 2:330–334, (1990).

Midthun, et al., "Reassortant rotaviruses as potential live rotavirus vaccine candidates," *J. of Virology,* 53(3):949–954, (1985).

Dimitrov, D.H., et al., "Detection of Rotaviruses by Nucleic Acid Hybridization . . . ," *J. of Infectious Diseases,* 152(2):293–300 (1985).

Flores, J., et al., "A DOT Hybridisation Assay for Detection of Rotavirus," *The Lancet,* 555–559 (1983).

McNeal, M., et al., "Active Protection against Rotavirus Infection of Mice . . . ," *Virology,* 191:150–157 (1992).

Ball, J., et al., "Immune Responses to Mucosal Pathogens and Novel Mucosal Vaccines," *Journal of Cellular Biochemistry,* Abstract J1–200:254.

Matson, D., et al., "Fecal Antibody Response to Syptomatic and Asymptomatic Rotavirus Infections," *J. of Infectious Diseases,* 167:577–83 (1993).

Michelangeli, F., et al., "Selective Depletion of Stored Calcium by Thapsigargin Blocks . . . ," *J. of Virology,* 3838–3847 (1995).

Sattar, S.A., et al., "Rotavirus inactivation by chemical disinfectants and antiseptics used in hospitals", *Can. J. Microbiol.* 29:1464–1469 (1983).

Vaughn, J.M., et al., "Inactivation of Human and Simian Rotaviruses by Ozone," *Appl. Env. Microbiol.* 53(a):2218–2721 (1987).

Estes, M., et al., "Rotavrus Stability and Inactivation," *J. gem. Virol.,* 43:403–409 (1979).

Berman, D., et al., "Inactivation of Simian Rotavirus SA11 by Chlorine, Chlorine Dioxide, and Monochloramine," Applied and Environmental Microbiology, 317–323 (1984).

Tan, J., et al., "Inactivation of a Rotavirus By Disinfectants," *Med. J. Aust.,* 1:19–23 (1981).

Chen, Y., et al., "Inactivation of Human and Simian Rotaviruses by Chlorine Dioxide," *Applied and Environmental Microbiology,* 1363–1366 (1990).

Matsui, S., et al., "Passive Protection against rotavirus–Induced Diarrhea by Monoclonal . . . ," *J. of Clin. Microbiology,* 780–782 (1989).

Zissis, G., et al., "Protection Studies in Colostrum–Deprived Piglets of a Bovine Rotavirus . . . ," *J. of Infectious Diseases,* 148(6):1061–1068 (1983).

Andrews, et al., "Vaccinia—rotavirus VP7 recombinants protect mice against rotavirus–induced diarrhoea," *Vaccine,* 10(3):137–200 (1992).

Au, K., et al., "A Subviral Particle Binding Domain on the Rotavirus Nonstructural Glycoprotein NS28," *Virology* 194:665–673 (1993).

Richardson, S., et al.,"Analysis of Homotypic and Heterotypic Serum Immune Responses to Rotavirus . . . ," J. of Clin. Microbiology, 31(2):337–385, (1993).

Cohen, et al., "Molecular Cloning of the Simian Rotavirus SA11," Double–Stranded RNA Viruses, International Symposium on Double Stranded RNA Viruses, held Oct. 5–10, 1982, St. Thomas, U.S. Virgin Islands.

Summers and Smith, "Manual of Methods for Baculovirus Vectors and Insect Cell Culture Procedures," Texas Agriculture Experiment Station, Bulletin 1555, first printing (1987), second printing (1988).

Ball, J., et al., "Age–dependent Diarrhea Induced by a Rotaviral Nonstructural glycoprotein," Science 272(5258):101–4 (1996).

Mason, H., et al., "Expression of Norwalk virus capsid protein in transgenic tobacco and potato and its immunogenicity in mice," *Proceedings of the National Academy of Sciences of USA,* 93:5335–5340.

Tian, T. et al., "The Rotavirus Nonstructural Glycoprotein NSP4 Possesses Membrane Destabilization Activity," *Journal of Virology,* 69(9):5763–5772 (1995).

Herrmann, J., et al., "Monoclonal Antibodies for Detection of Norwalk VirusAntigen in Stools," *Journal of Clinical Microbiology,* 33(9):2511–2513 (1995).

Matson, D., et al., "Assessment of epitope–blocking assays for measuring antibody to rotavirus," *Journal of Virological Methods,* 48:293–300 (1994).

O'Ryan, M., et al., "Anti–Rotavirus G Type–Specific and Isotype–specific Antibodies in Children with Natural Rotavirus Infections," *The Journal of Infectious Diseases,* 169:504–511 (1994).

Offit, P., et al., "Noninfectious Rotavirus (Strain RRV) Induces an Immune Response in Mice Which Portects against Rotavirus Challenge," *Journal of Clinical Microbiology,* 27(5):885–888 (1989).

Both, G., et al., "Serotype–specific glycoprotein of simian 11 rotavirus Coding assignment and gene sequence," *Proc. Natl. Acad. Sci. USA,* 80:3091–3095 (1993).

Miyamoto, C., et al., "Production of Human c–myc Protein in Insect Cells Infected with a Baculovirus Expression Vector," *Molecular and Cellular Biology,* 5(10):2860–2865 (1985).

Mason, B., et al., "Biochemical Mapping of the Simian Rotavirus SA11 Genome," *Journal of Virology,* 46(2):413–423 (1983).

Boyle, J., et al., "RNA–Binding Proteins of Bovine Rotavirus," *Journal of Virology,* 58(2):561–568 (1986).

Imai, M., et al., "Molecular cloning of double–stranded RNA virus genomes," *Proc. Natl. Acad. Sci. USA,* 80:373–377 (1983).

Lin., M., et al., "Diagnosis of Rotavirus Infection with Cloned cDNA Copies of Viral Genome Segments," *Journal of Virology,* 55(2):509–512 (1985).

Sabara, M., et al., "Identification of a Bovine Rotavirus Gene and Gene Product Influencing Cellular Attachment," *Journal of Virology,* 51(2):489–496 (1984).

Tian, P., et al., "The Nonstructural Glycoprotein of Rotavirus Affects Intracellular Calcium Levels," *Journal of Virology,* 68(1):251–257 (1994).

Lima, A., et al., "Effects of *Clostridium Difficle* Toxins A and B in Rabbit Small . . . ," Infection and Immunity 56(3):582–588 (1988).

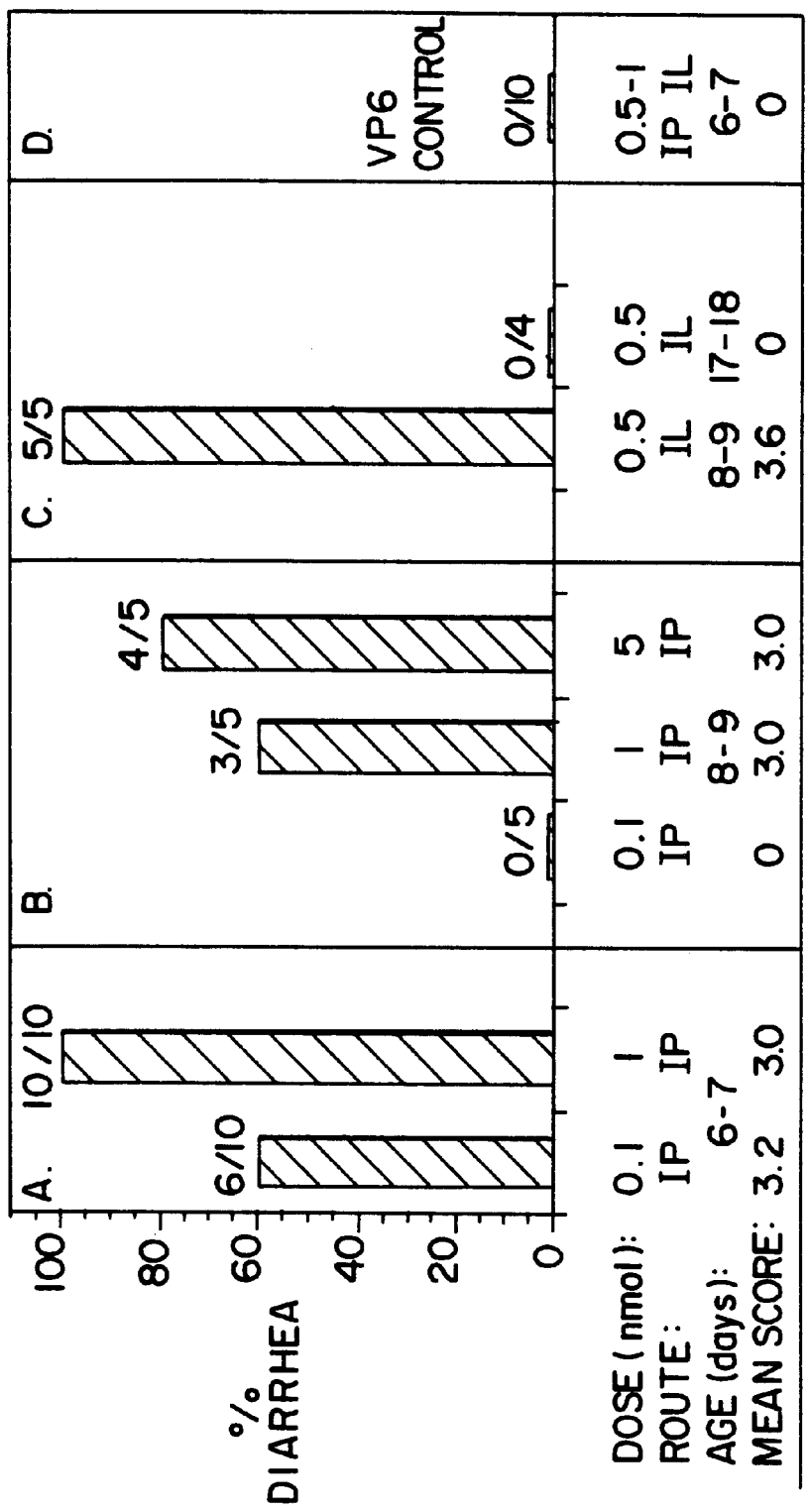

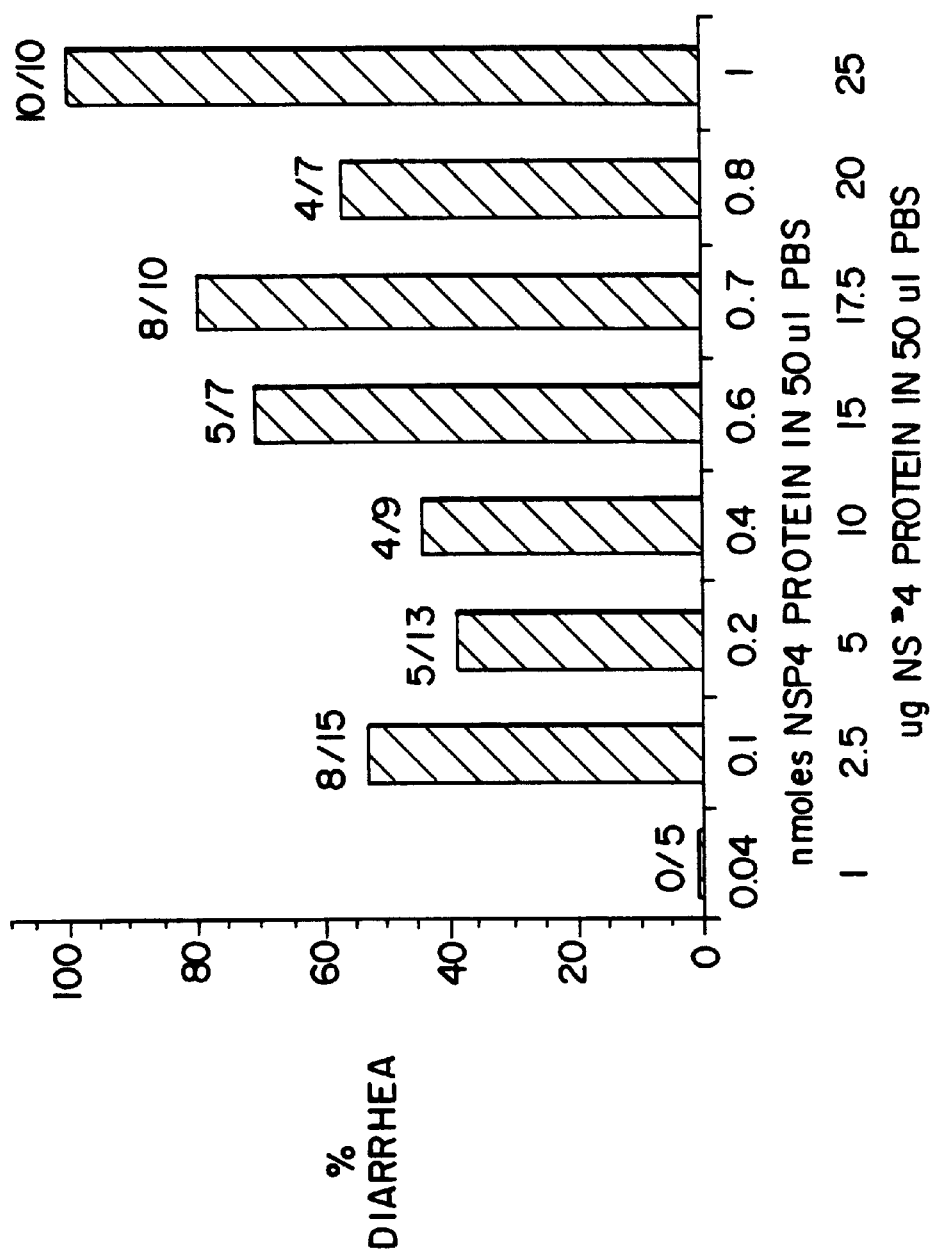

FIG. 4A

CD1 MICE — % DIARRHEA vs nmol CROSS-LINKED NSP4 114-135 PEPTIDE

Balb/C MICE — % DIARRHEA vs nmol CROSS-LINKED NSP4 114-135

- 0.1: 2/6 (~33%)
- 10: 4/4 (100%)
- 50: 4/5 (~88%)
- 100: 5/5 (~98%)

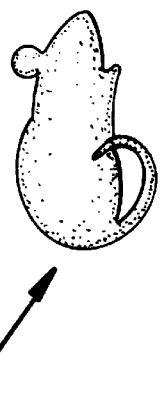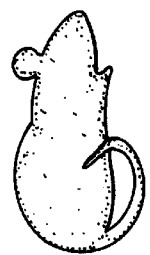
FIG. 5

FIG. 7

```
       1                                                                                  
OSU-a  1   MDKLADLNYT  LSVITLMNDT  LHSIIQDPGM  AYFPYIASVL  TVLFTLHKAS
OSU-v  1   MDKLADLNYT  LSVITLMNDT  LHSIIQDPGM  AYFPYIASVL  TVLFTLHKAS

51  IPTMKIALKT  SKCSYKVIKY  CMVTIINTLL  KLAGYKEQVT  TKDEIEQQVD
       51  IPTMKIALRT  SKCSYKVIKY  CIVTIINTLL  KLAGYKEQVT  TKDEIEQQMD

101 RIIKEMRRQL  EMIDKLTTRE  IEQVELLKRI  HDKLAARSVD  AIDMSKEFNQ
       101 RIVKEMRRQL  EMIDKLTTRE  IEQVELLKRI  HDKLVVRPVD  AIDMSKEFNQ

151 KNIRTLDEWE  SGKNPYEPSE  VTASM
       151 KNIRTLDEWE  SGKNPYEPSE  VTASM
```

ROTAVIRUS ENTEROTOXIN NSP4 AND METHODS OF USING SAME

This application is the National Stage of International Application No. PCT/US96/10523, filed on Jun. 14, 1996, which claims the benefit of U.S. Provisional Application No. 60/000,220, filed Jun. 14, 1995 and a CIP of U.S. Application No. 08/628,014, filed Apr. 4, 1996, now abandoned

BACKGROUND OF THE INVENTION

1. Field of the Invention

This invention relates to the viral enterotoxin NSP4 and to methods for using it, or antibodies/antisera thereto, as diagnostic agents, vaccines and therapeutic agents for the detection, prevention and/or treatment of rotaviral disease, for the prevention of stunted growth in animals and children caused by rotaviral infection and for the treatment of cystic fibrosis. This invention also relates to methods and animal models for 1) the screening for viral enterotoxins, 2) the detection of viral enterotoxins and 3) the identification of viral enterotoxins.

2. Related Technology

Rotaviruses are the leading cause of severe, life-threatening viral gastroenteritis in infants and animals (1) and are associated with sporadic outbreaks of diarrhea in elderly (2) and immunocompromised patients (3). These viruses have a limited tissue tropism, with infection primarily being restricted to cells of the small intestine (4). Rotavirus infections also cause morbidity and mortality in many animal species. Moreover, the outcome of infection is age-related; although rotaviruses may infect individuals and animals of all ages, symptomatic infection (i.e., diarrhea) generally occurs in the young (6 months–2 years in children, and up to 14 days in mice), and the elderly.

Age-related host factors which may influence the outcome of infection have been proposed to include 1) differences in the presence/quantity of virus-binding receptors on mature villus epithelial cells, 2) virus strains with a specific spike protein (VP4), 3) passive immunity acquired by maternal antibody or in colostrum, and 4) reduced levels of proteases in the young.

Disease resulting from rotavirus infection in mice has been studied more extensively than in any other species and an age restriction of disease has been reported by several investigators (5). Only mice less than 14 days of age develop diarrhea following oral inoculation of murine rotavirus, and the peak age at which animals are most likely to develop diarrhea (6–11 days) corresponds to the age when rotavirus can bind to mouse enterocytes (6). Treatment of 8 day old mice with cortisone acetate which promotes premature maturation of intestinal epithelial cells, results in a reduced susceptibility to rotavirus-induced diarrhea, although the mice can still be infected (7). These data were interpreted to suggest that the capacity of murine rotaviruses to induce diarrhea in young, but not adult mice, is due to the quantity of rotavirus-binding receptors on the surface of villus epithelial cells in the young mouse intestine.

When compared to rotavirus infections in other species, rotavirus infections in mice show minimal histologic alterations. That is, villus blunting is limited and transient, and crypt cell hyperplasia is not present. In addition, the loss of villus tip epithelial cells is more limited in mice than in other animals. Instead, vacuolization of enterocytes on the villus tips is a predominant feature in symptomatic rotavirus infection in mice and virus replication may be abortive (8). The lack of extensive pathologic alterations in the mouse intestine during symptomatic infections has remained a puzzle; one interpretation of this phenomenon is that a previously unrecognized mechanism of diarrhea induction may be active in symptomatic rotavirus infection in mice.

Despite the prevalence of rotavirus infections and extensive studies in several animal models and many advances in understanding rotavirus immunity, epidemiology, replication and expression, rotavirus pathogenesis, specifically, the mechanism of diarrhea induction, remains poorly understood. Proposed pathophysiologic mechanisms by which rotaviruses induce diarrhea following viral replication and viral structural protein synthesis include malabsorption secondary to the destruction of enterocytes (9), disruption of transepithelial ion homeostasis resulting in fluid secretion (10), and local villus ischemia leading to vascular damage and diarrhea (11). However, these proposed mechanisms do not explain cases of rotavirus-induced diarrhea observed prior to, or in the absence of, histopathologic changes (12).

On the other hand, the pathophysiology of bacterial-induced diarrhea based on interactions with intestinal receptors and bacterial enterotoxins is well understood (13). The heat-stable toxin A and the heat-labile toxin of *E. coli*, and guanylin (an endogenous, 15 amino acid intestinal ligand originally isolated from rat jejunum) induce diarrhea by binding a specific intestinal receptor, increasing cAMP or cGMP, and activating a cyclic nucleotide signal transduction pathway (14). The net effect of these bacterial toxins is to increase $Cl^-$ secretion, and decrease $Na^+$ and water absorption.

Previous studies in insect cells indicated that a receptor-mediated phospholipase C pathway is associated with the increases in $[Ca^{2+}]_i$, following exogenous treatment of cells with NSP4 or NSP4 114–135 peptide (15). The rotavirus nonstructural ER glycoprotein, NSP4, has been shown to have multiple functions including the release of calcium from the endoplasmic reticulum (ER) in SF9 insect cells infected with recombinant baculovirus containing the NSP4 cDNA (15, 16). In addition, NSP4 disrupts ER membranes and may play an important role in the removal of the transient envelope from budding particles during viral morphogenesis (unpublished data). NSP4 114–135, a 22 aa peptide of NSP4 protein, has been shown to be capable of mimicking properties associated with NSP4 including being able to (i) mobilize intracellular calcium levels in insect cells when expressed endogenously or added to cells exogenously (15, 16), and (ii) destabilize liposomes. (unpublished data).

Expression of NSP4 in insect cells increased $[Ca^{2+}]_i$ levels from a subset of the thapsigargin-sensitive store (ER) (15). The $[Ca^{2+}]_i$ mobilized by NSP4 or the NSP4 114–135 peptide was blocked by a phospholipase C inhibitor, the U-73122 compound, suggesting that a receptor-mediated pathway is responsible for the calcium release from the ER induced by NSP4 (15).

BRIEF DESCRIPTION OF THE INVENTION

This invention stems from the discovery of the first known viral enterotoxin, rotavirus NSP4, previously called NS28, which encodes a viral toxin capable of inducing intestinal secretion through a heretofore unknown signal transduction pathway to cause diarrheal disease.

This paper reports the fortuitous discovery that the rotavirus nonstructural ER glycoprotein, NSP4, induces an age-dependent diarrhea in two rodent models. Induction of diarrhea following administration of this protein alone was completely unexpected because infection with rotavirus was not involved. Characterization of the parameters of these new models of rotavirus-induced diarrhea demonstrates that this enteric viral-encoded protein is an enterotoxin, similar to bacterial enterotoxins which are wellknown to induce diarrhea by stimulating signal transduction pathways following interaction with specific intestinal receptors. The ordinary practitioner will appreciate that these new findings on NSP4-induced diarrheal disease and the data presented herein support several novel therapeutic and preventive approaches to rotavirus-induced disease.

It is also reported here that a synthetic peptide corresponding to aa 114–135 of SA11 NSP4 also induces an age-dependent diarrhea in young mice comparable to NSP4 when administered by the IP and IL route. Since the NSP4 114–135 peptide was readily available in large amounts in pure form, we studied the response to the peptide in detail. The response to the peptide was specific as shown by 1) lack of response to control peptides, 2) blocking with peptide-specific antibody, and 3) a mutated peptide (differing by only a single residue) alone failed to induce the response. The concentration of peptide required for disease induction was considerably higher than that needed for a response to the protein. Because the entire protein possesses more potent activity than the peptide, other peptides from this protein which have the same effect are also included in the present invention.

We have shown an analogous age dependence in the induction of diarrhea with purified NSP4 protein and NSP4 114–135 peptide. Mice were most sensitive to the effects of the protein or peptide at 6–7 days of age. Diarrhea induction by NSP4 or NSP4 114–135 decreased as the age of the animal increased, regardless of the route of administration. Hence the observed diarrhea in this study mimics the properties of symptomatic infection observed in experimental and natural rotavirus infection.

We have also shown that inoculation of NSP4 114–135 peptide-specific antiserum prior to IP delivery of peptide results in a dramatic reduction of disease. (90% reduction in disease).

We have also shown that diarrheal disease in pups born to dams immunized with the NSP4 114–135 peptide is significantly reduced in severity, duration, and in the number of pups with diarrhea.

We have also shown that post-infection administration of NSP4-specific antibody significantly reduces diarrheal disease.

These data, showing that NSP4 protein or NSP4 114–135-specific antibodies are sufficient to block the induction or severity of diarrhea, demonstrate that NSP4 and/or NSP4 114–135 and/or antibodies specific thereto will be useful as vaccines and as therapeutic agents. Additionally, new drugs can now be developed to block or minimize the effects of interaction of NSP4 with its receptor or the effects of the disruption of the calcium homeostasis in affected cells.

In addition, animals given peptide twice (at a two day interval) showed a rapid onset of severe diarrhea followed by stunted growth. The weight of these animals was 20–30% lower for three weeks after administration of peptide.

Based on our results on NSP4-induced diarrhea in mice and rats, we have proposed a model in which two intestinal receptors are required for symptomatic rotavirus infection. One receptor binds rotavirus particles resulting in virus entry and gene expression, but not necessarily disease, whereas the second receptor is NSP4-specific. Additionally, while the receptor for rotavirus infection is maintained with age, allowing the adult mouse (34–35 days old) to replicate and excrete virus, the NSP4 fully functional receptor is not maintained with developmental aging, so disease is not observed. In addition, disease is not seen in adolescent mice (17–18 days old) because the colon of these animals can absorb fluid secreted in the small intestine.

We have shown that NSP4 114–135 promotes and augments cAMP-dependent Cl⁻ secretion in mouse intestinal mucosa and induces diarrhea in rodents in a time frame similar to $ST_B$ (about 3 hrs). The electrophysiological data show that NSP4 induces calcium increases in the intestines of mice in an age-dependent manner and these increases in calcium result in chloride secretion as measured by short-circuit currents. Direct addition of cross-linked NSP4 114–135 to mouse ileal mucosal sheets resulted in a rise in current, similar to that evoked by the calcium agonist, carbachol. In addition to the age-dependence, induction of chloride secretion from intestinal mucosal sheets was site-dependent. Zero to minimal responses were observed when mouse jejunum, duodenum or colon tissue was employed, and maximum responses were induced when the ileum was utilized. These results support our model of NSP4-induced diarrhea.

Our data show that NSP4 stimulation of a $Ca^{2+}$-dependent signal transduction pathway, resulting in disruption of normal intestinal epithelial transport, is similar to that reported for guanylin and the heat-stable enterotoxins. Based on the enteropathogenic similarities in intestinal secretion with those reported for guanylin and the heat-stable enterotoxins, NSP4 can be considered a viral enterotoxin.

We have also shown that administration of virus or peptide to 5–7 day old CFTR knock-out mice—mice homozygous for the mutation in the CFTR chloride channel coding region that causes Cystic Fibrosis—results in diarrhea in 100% of the cases.

We have also shown that administration of HIV gp160 to 6–7 day old Balb/C mice causes diarrhea in 100% of the cases.

In accordance with the foregoing and with the disclosure that follows, it is an object of the present invention to provide a method for the screening and identification of viral enterotoxins associated with rotavirus and other gastroenteritis viruses, such as caliciviruses, astroviruses, enteric adenoviruses, coronaviruses, and parvoviruses, including administering expressed proteins or peptides or synthetic peptides of such viruses to animals and monitoring the animals for diarrhea. For the purpose of this and other objects of the invention, human volunteers shall be considered to be within the scope of "animals." It is a further object of the present invention to provide methods for the screening and identification of new viral enterotoxins including administration of expressed proteins or peptides or synthetic peptides to CD1 mice, Balb/C mice and/or Sprague-Dawley rats and monitoring for diarrhea.

To the extent that the meaning of the term "diarrhea-genic viral protein" may be construed to differ from the meaning of the term viral enterotoxin, if the term "diarrhea-genic viral protein" is substituted for the term viral enterotoxin, the subject matter of this and all following objects and all claims is also considered to be within the scope of the invention, and fully described for all purposes.

It is another object of the present invention to provide methods for the screening for and identification of viral enterotoxins associated with rotavirus and other gastroenteritis viruses, such as caliciviruses, astroviruses, enteric adenoviruses, coronaviruses and parvoviruses, including in vitro administration of virus, viral proteins or peptides thereof to intestinal mucosa tissues or to cells and monitoring chloride secretion and/or intracellular calcium levels and/or cAMP levels.

It is another object of the present invention to provide a method for the screening for and identification of viral enterotoxins associated with viruses that are not known as diarrhea or gastroenteritis virus, but that are associated with diarrhea as a consequence of infection. Without limiting the invention, examples include human immunodeficiency virus (HIV) and cytomegalovirus (CMV). This method includes administering expressed proteins or peptides or synthetic peptides of a selected virus to animals and monitoring the animals for diarrhea.

It is another object of the present invention to provide methods for the screening for and identification of viral enterotoxins associated with other viruses associated with diarrhea, including HIV and CMV, including in vitro administration of virus, viral proteins or peptides thereof to intestinal mucosa tissues or to cells and monitoring chloride secretion and/or intracellular calcium levels and/or cAMP levels.

It is another object of the present invention to provide a method for treatment of diarrheal disease, including reducing the severity of diarrhea, caused by viral infection, including administering antibodies to viral enterotoxins to a subject with diarrhea or known, or suspected to be infected by or to have been exposed to a gastroenteritis virus. For the purpose of this invention, antibodies shall mean polyclonal and monoclonal antibodies unless otherwise indicated. Methods for the preparation of polyclonal and monoclonal antibodies to any protein or peptide are well known to the practitioner having ordinary skill in the art.

It is another object of the present invention to provide a method for the prevention or amelioration of diarrhea caused by rotavirus infection including administration of antibodies to NSP4 protein or peptides thereof, including but not limited to NSP4 114–135 and NSP4 120–147. As rotavirus infection is transmitted rapidly, this method is considered to include the prevention or amelioration of disease following exposure to a known infected person, for example in day care centers and in hospitals.

For the purpose of this invention, the term "compound comprising amino acids in a sequence corresponding to NSP4 114–135" shall mean a compound which has within it a sequence of amino acids corresponding to the sequence of NSP4 114–135, including NSP4 114–135 and the NSP4 protein. For the purpose of this invention, the term "compound comprising amino acids in a sequence corresponding to NSP4 120–147" shall mean a compound which has within it a sequence of amino acids corresponding to the sequence of NSP4 120–147, including NSP4 120–147 and the NSP4 protein. For the purpose of this invention, the term "derivative" shall mean any molecules which are within the skill of the ordinary practitioner to make and use, which are made by derivatizing the subject compound, and which do not destroy the activity of the derivatized compound. Compounds which meet the foregoing criteria which diminish, but do not destroy, the activity of the derivatized compound are considered to be within the scope of the term "derivative." Thus, according to the invention, a derivative of a compound comprising amino acids in a sequence corresponding to the sequence of NSP4 114–135 or NSP4 120–147, need not comprise a sequence of amino acids that corresponds exactly to the sequence of NSP4 114–135 or NSP4 120–147, so long as it retains a measurable amount of the activity of the NSP4 114–135 or NSP4 120–147 peptide.

It is another object of the present invention to provide monoclonal antibodies to NSP4 protein, to NSP4 114–135 peptide, to NSP4 120–147 peptide, and to other peptides of NSP4.

It is another object of the present invention to provide a method for the prevention of decreased growth rates caused by rotavirus infection including use of the NSP4 protein or peptides thereof, including but not limited to NSP4 114–135 and/or NSP4 120–147, as a treatment for or vaccine against rotavirus diarrhea.

It is another object of the present invention to use the NSP4 protein or peptides thereof, including but not limited to NSP4 114–135 and NSP4 120–147, to identify and/or characterize a new intestinal receptor whose signaling induces secretion.

It is another object of the present invention to provide methods for the identification and use of compounds, such as small molecule inhibitors, to bind the active domain of NSP4 or other viral enterotoxins to prevent, ameliorate or stop diarrheal disease. For the purpose of this invention, small molecule inhibitors shall mean any ligand that can bind with high affinity to a target molecule, thereby inhibiting the target molecule's activity. Small molecule inhibitors include, but are not limited to, peptides, oligonucleotides, amino acids, derivatized amino acids, carbohydrates, and organic and inorganic chemicals. Libraries of small molecule inhibitors are available to the practitioner either according to known methods, or commercially. Accordingly, this method includes identifying a viral enterotoxin, screening the purified enterotoxin against one or more random small molecule libraries, for example, a random peptide library, a random oligonucleotide library, or a pharmaceutical drug library, and identifying those small molecules that bind with high affinity to the viral enterotoxin.

Another method for identifying small molecule inhibitors includes the steps of identifying viral enterotoxins, determining the high resolution structure of these proteins and/or peptides thereof, determining the active domain(s) and designing small molecule inhibitors which bind with high affinity to the active domain(s). Another method includes identifying viral enterotoxins, identifying the intestinal receptor which binds the viral enterotoxin, and designing small molecule inhibitors which competitively bind the receptor, without inducing secretion.

It is another object of the present invention to provide a method for the design of new drugs for the prevention of diarrhea and/or $Ca^{2+}$ mediated intestinal secretion including identifying the intracellular pathway by which $[Ca^{2+}]_i$ is increased and making compounds which inhibit any step in the pathway. Specifically, this method includes identifying the molecules active in the signalling pathway and identifying compounds which inhibit their activity. Such compounds will include but not be limited to small molecule inhibitors which block binding of NSP4 to its receptor, blocking of G protein mediated or other signal transduction secondary messengers and pathways which lead to chloride secretion or diarrhea.

It is another object of the present invention to provide a method for the diagnosis of rotavirus infection including the detection of NSP4 in stools of individuals with diarrhea. Detection of peptides of NSP4 is considered to fall within the scope of detection of NSP4.

It is another object of the present invention to provide a method for the diagnosis of rotavirus infection including the detection of antibodies to NSP4 in the sera or stools of individuals with diarrhea.

It is another object of the present invention to provide a vaccine comprising the NSP4 protein or peptides thereof, including but not limited to NSP4 114–135 and NSP4

120–147, to induce the formation of protective active or passive antibodies.

It is another object of the present invention to provide a vaccine comprising a toxoid form of the NSP4 protein, including but not limited to formaldehyde inactivated NSP4 to induce the formation of a protective immune response.

It is another object of the present invention to provide vaccines against gastroenteritis viruses, including rotaviruses, caliciviruses, astroviruses, enteric adenoviruses, coronoviruses and parvoviruses, including viral enterotoxins which induce the diarrhea associated with viral infection.

It is another object of the present invention to provide methods for the identification of potential vaccines against gastroenteritis viruses, including screening for viral enterotoxins, raising antibodies against any identified possible enterotoxins, and determining whether the antibodies protect against disease caused by the virus.

It is another object of the present invention to provide a method to monitor vaccine efficacy or protective immunity by determining the immune response to NSP4 protein and/or to peptides thereof.

It is another object of the present invention to provide a method for immunization against rotavirus infection comprising administering to a subject a vaccine including the NSP4 protein or peptides thereof, including but not limited to NSP4 114–135 and NSP4 120–147 peptides.

It is another object of the present invention to provide a method for immunization against rotavirus infection comprising administering to a subject a vaccine comprising a toxoid form of the NSP4 protein.

It is another object of the present invention to identify key residues in NSP4 responsible for its ability to induce diarrhea and thus to identify specific amino acid sequences associated with avirulence. Having done this, gene 10 from these avirulent viruses may be used to select and produce reassortment viruses that contain a gene 10 that confers an avirulent phenotype which can be used as live attenuated reassortment virus vaccine candidates.

It is another object of the present invention to provide a method of identifying a virulent strain of rotavirus by determining the amino acid sequence of the NSP4 protein of the strain.

It is another object of the present invention to provide a method of passive immunization against rotavirus infection including administering to an expectant mother a vaccine including the NSP4 protein or peptides thereof, including but not limited to NSP4 114–135 and NSP4 120–147.

It is another object of the present invention to provide a method for the intentional induction of intestinal secretion including administration of the NSP4 protein or peptides thereof, including but not limited to NSP4 114–135 and NSP4 120–147.

It is another object of the present invention to provide a method for the treatment of cystic fibrosis including administration of NSP4 protein or peptides thereof, including but not limited to NSP4 114–135 and NSP4 120–147, to enhance fluid secretion.

It is another object of the present invention to provide a method for the treatment of cystic fibrosis comprising administering NSP4 or derivatives or new molecules that act like NSP4 to enhance secretion through the same mechanism NSP4 uses.

It is another object of the present invention to provide a new laxative including the NSP4 protein or peptides thereof, including but not limited to NSP4 114–135 and NSP4 120–147.

It is another object of the present invention to provide methods for the screening of antiviral compounds, compositions and/or treatments and/or the evaluation of vaccine efficacy, including administering viruses, viral proteins or peptides thereof to one or more of three new animal models for diarrheal virus infections, the CD1 mouse, the Balb/C mouse and the Sprague-Dawley rat.

DESCRIPTION OF THE DRAWINGS

FIG. 1A Rotavirus NSP4 protein induces diarrhea in CD1 mice. 0.1 to 5 nmols (2–100 μM) of purified NSP4 was administered by the IP or IL routes to 6–7, 8–9 and 17–18 day old CD1 pups. Rotavirus protein VP6 was used as the control in 6–7 day old animals, the most sensitive. The dose and route of the proteins, age of the animals, and mean diarrhea score (mean score) are indicated on the bottom of the graph. The Y axis displays the % diarrhea. Above each column is the number of responders (mice with diarrheal disease) over the total number of animals tested.

FIG. 1B IP administration of NSP4 induces diarrhea in 6–7 dav old CD-1 pups. 0.04 to 1.0 nmols (1–25 μg) of purified NSP4 protein was administered to 6–7 day old CD1 pups by the IP route. The dose administered, in nanomoles and in micrograms, is shown on the X-axis. The percentage of pups that display diarrhea in response to the administered dose is shown on the Y-axis. Above each column the number of responders (pups with diarrhea) over the total number of animals receiving treatment is shown.

FIG. 2A Diarrheal response in CD1 mice following IP administration of NSP4 114–135 peptide. Young (6–7 day) mouse pups were injected with various doses of peptide (x axis) and monitored for disease. The number of responders over the total number animals tested is shown above each column. With the CD1 mice, 0.1–50 nmol (2 μM-1 mM) of peptide elicited similar responses (30–40% diarrhea induction); and 100–400 nmols (2–8 mM) of peptide elicited comparative responses with 60–70% of the animals sick. A slight increase in disease was noted with 500 nmol (10 mM) of peptide. No diarrhea was induced with 0.001 nmol of peptide (data not shown).

FIG. 2B Diarrheal response in Balb/C mice following IP administration of NSP4 114–135 peptide. Young (6–7 day) mouse pups were injected with various doses of peptide (x axis) and monitored for disease. The number of responders over the total number animals tested is shown above each column. With the Balb/C pups, diarrhea induction was seen in 100% of the animals with 50 nmol (1 mM) of peptide indicating the inbred animals are more sensitive to the effect of the NSP4 peptide.

FIG. 3A IP delivers of NSP4 114–135 peptide induce an age-dependent diarrhea in CD1 mice and Sprague-Dawley Rats. Different age outbred mice and rats were inoculated (IP) with NSP4 114–135 peptide and evaluated for disease. The age and species of the pups, dose of the synthetic peptide and indication of whether peptides were unlinked or cross-linked are indicated on the bottom of the graph. The dose of the IP delivered peptide varied with the age of the animals, i.e., older animals received a higher dose to control for the differences in body weight. The Y axis indicates the % diarrhea and above each column is indicated the number of responders over the total number of animals inoculated. The peptide was diluted in sterile PBS and evaluated for sterility. A final volume of 50 μl per dose was used. Analogous to the effects of purified NSP4, additional symptoms included lethargy and coldness to the touch.

FIG. 3B IL delivery of NSP4 114–135 peptide induce an age-dependent diarrhea in CD1 mice and Spraque-Dawley Rats. Different age outbred mice and rats were inoculated (IL) with NSP4 114–135 peptide and evaluated for disease. The age and species of the pups, dose of the synthetic peptide and indication of whether peptides were unlinked or cross-linked are indicated on the bottom of the graph. The Y axis indicates the % diarrhea and above each column is indicated the number of responders over the total number of animals inoculated. The peptide was diluted in sterile PBS and evaluated for sterility. A final volume of 50 μl per dose was used. Analogous to the effects of purified NSP4, additional symptoms included lethargy and coldness to the touch.

FIG. 4 Dose Response for Cross-Linked NSP4 Peptide Delivered IP to 6–7 day old CD1 and Balb/C Mice. The NSP4 114–135 peptide was cross-linked to itself with glutaraldehyde and dialyzed against sterile PBS prior to IP delivery to CD1 and Balb/C mice. The number of responders over the total number of animals inoculated is shown above each column. The disease response to the cross-linked peptide was seen at lower doses when compared to the peptide alone. Additional symptoms included lethargy and coldness to the touch.

FIG. 5 illustrates the experimental designs used to test the ability of NSP4 114–135 to induce protective immunity from infectious rotavirus challenge and to test the ability of NSP4-specific antibody to mitigate rotavirus diarrhea following infection. The left hand side of the figure illustrates that mouse dams were immunized with NSP4 peptide or with control peptide and then bred. Pups born to the dams were orally challenged with virulent rotavirus at 6–7 days. The right hand side of the figure illustrates how pups born to non-immunized dams were first orally challenged with virulent rotavirus, followed by oral gavage of NSP4-specific or control antisera. The results of these experiments are set forth in Tables 5 and 6.

FIG. 6 illustrates the results from an experiment to study the differences in weight and growth between normal animals and animals suffering from NSP4 114–135-induced diarrhea.

FIG. 7 Amino acid sequence comparison of NSP4 from OSU attenuated and OSU virulent virus. The amino acid sequence of the NSP4 protein of OSU-a (a porcine rotavirus, tissue culture attenuated, avirulent strain), top line, is compared to the amino acid sequence of the NSP4 protein of OSU-v (a porcine rotavirus, virulent strain), bottom line. Positions at which the two sequences are different are shown in bold.

DETAILED DESCRIPTION OF THE INVENTION

Materials and Methods

EXAMPLE 1

Figure 2A:
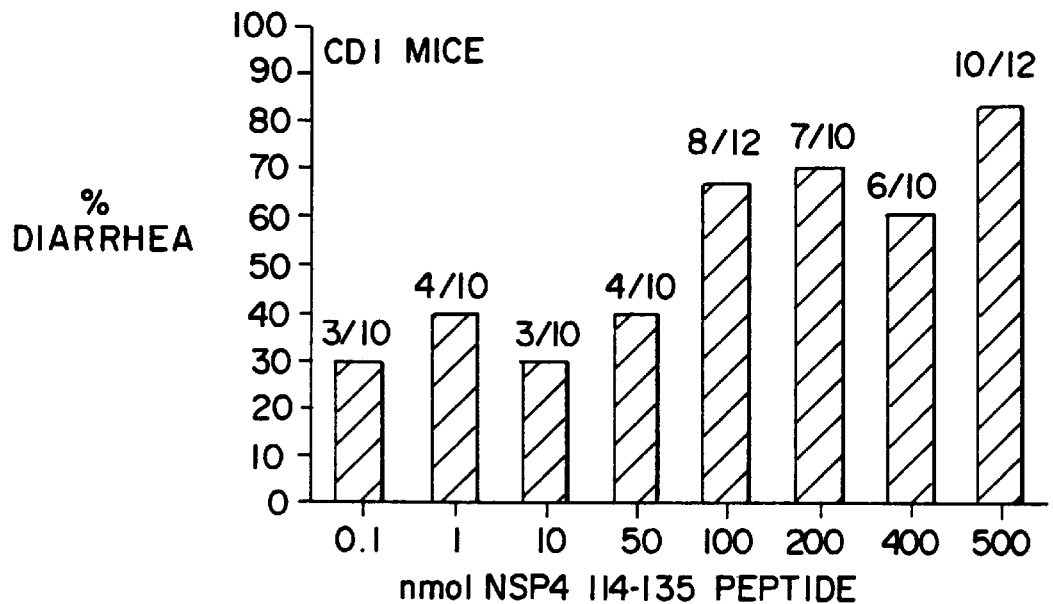

NSP4.

NSP4 was purified from recombinant-baculovirus pAC461-G10 infected *Spodoptera frugiperda* (Sf9) cells expressing gene 10 by FPLC on a QMA anion exchange column as previously described (15, 16), and with an additional affinity purification step on a column containing anti-NSP4 antibodies. Different NSP4 preparations of ≧70% and 90% purity gave the same biologic results. The protein was sterile based on bacteriologic culturing in L-broth incubated at 37° C. for one week, and lacked endotoxin based on testing by the limulus amebocyte lysate (LAL) assay (17). VP6 was purified to >95% purity from recombinant-baculovirus pAc461/SA11-G6 infected Sf9 cells by gradient centrifugation as previously described (18). Both proteins were lyophilized and diluted in sterile PBS to a final volume of 50 μl per dose, regardless of the route of administration.

EXAMPLE 2

Synthetic Peptides.

Synthetic NSP4-specific and control peptides utilized in this study were originally selected based on algorithms which predict surface potential (19), turn potential (Pt) (20), and amphipathic structure (21). A block length of 11 was used and an amphipathic score (AS) of 4 was considered significant. We selected sequences with unusually high predicted propensities for folding into amphipathic helices and reverse turns, because small peptides which typically lack any folding pattern in an aqueous environment can fold into an ordered secondary structure resembling the nascent protein if the structural propensity is high (22).

Peptide sequences used in this study include: NSP4 114–135 (23), (DKLTTREIEQ VELLKRIYDKLT, SEQ ID NO. 1), AS=35; a peptide from the amino-terminus of NSP4, NSP4 2–22 (EKLTDLNYTLSVITLMNNTLH, SEQ ID NO. 2), AS=14; an extended highly amphipathic peptide, NSP4 90–123 (TKDEIEKQMDRVV KEMRRQLEMIDKLTTREIEQ, SEQ ID NO. 3) AS=71; a mutated NSP4 114–135 peptide, mNSP4 131K (DKLTTREIEQVELLKRI<u>K</u>DKLT, SEQ ID NO. 4) AS=31; and a peptide from the COOH— terminus of the Norwalk virus capsid protein having a centrally located tyrosine residue (24), NV 464–483 (DTGRNLGEFKAYPDGFLTCV, SEQ ID NO. 5) AS=41 (table 1), and NSP4 120–147 (EIEQVELLKRIYDKLTVQTTGEIDMTKE, SEQ ID NO.6) AS=35.0.

All peptides were synthesized by the University of Pittsburgh Peptide Core Facility employing Fmoc chemical strategy and standard protocols (25). Coupling and deblocking efficiencies were monitored by the ninhydrin colorometric reaction (26). Peptides were cleaved from their solid resin support and separated from organic contaminants by multiple cold ether extractions, and conventional gel filtration chromatography (Sephadex G-25). The final peptide product was characterized by reverse-phase HPLC (Deltapak C4, Waters) and plasma desorption mass spectroscopy (27). Only those peptides with the correct theoretical mass and 90% or greater full-length product were employed in these studies. Prior to use, peptides were further purified either by HPLC on a semi-preparative, reverse-phase C18 column (Bondapak, Waters) or by multiple elutions from a conventional gel filtration column (1.5 mm×40 mm). Peptide purity was confirmed prior to inoculations by gel filtration chromatography (Protein-Pak 60 column, 10 μm, Waters) on a Waters HPLC unit. The elution profiles were monitored by UV absorption (Lambda-Max LC-spectrophotometer, Waters) at 220 nm and recorded by a 745 Data Module (Waters). The elution buffer was PBS, pH 7.2, and the flow rate 0.5 ml/min. Sterility was confirmed as described for NSP4 protein.

EXAMPLE 3

Glutaraldehyde Cross-linking of Synthetic Peptides.

In some cases, peptides were cross-linked to themselves or to the carrier protein, keyhole limpet hemocyanin (KLH), by glutaraldehyde in a single-step coupling protocol (28). Briefly, the peptide immunogen was coupled to KLH at a ratio of 100 nmol peptide: 1 nmol KLH or to itself at a 1:1 ratio by the addition of glutaraldehyde to a final concentration of 0.4%. The reaction was quenched by the addition of 1M glycine ($C_f$=20 mM). The cross-linked peptides were extensively dialyzed against sterile PBS prior to use.

EXAMPLE 4
Antibody Production.

NSP4 114–135 peptide-specific antiserum was generated in CD1 mice and New Zealand white rabbits by immunization with peptide cross-linked via glutaraldehyde to the protein carrier KLH, as described above. The first inoculum was emulsified in Freund's complete adjuvant(Gibco), whereas all subsequent inoculations were prepared in incomplete Freunds adjuvant. Rabbits were injected intramuscularly (IM, once in each hip) and subcutaneously (SC) across the back of the neck. Boosting doses of emulsified antigen (100 nmol of peptide) were done every 4 wk. for a total of 5 immunizations. Mice were immunized every three weeks by the IM, SC and IP routes. Preimmunization and postimmunization sera were evaluated by peptide ELISAs (titer of 400–3200) as previously described (29) and by Western blot analyses.

EXAMPLE 5
IP and IL Administration of Protein and Peptides.

Purified NSP4 protein, peptide alone, or cross-linked to itself, were administered to young (6–10 days) and older (11–25 days) outbred CD1 or inbred Balb/C mice, and outbred Sprague-Dawley rats by the intraperitoneal (IP), intraileal (IL), intramuscular (IM), subcutaneous and oral routes. The peptide or protein inocula were diluted in sterile PBS to a final volume of 50 µl per does, regardless of the route of administration or inoculum. A 30 G needle was employed for the IP and IL delivery of the inocula. Peptide was delivered orally to young mice by gavage using a PE-10 polyethylene flexible tubing (Intramedic, Becton Dickinson) and food coloring. For the surgical introduction of the peptide or protein via the IL route, animals were anesthetized with isofurane (Anaquest), a small incision was made below the stomach, the inocula were directly injected into the upper ileum, and the incision was sealed with polypropylene sutures (PROLENE 6-0, Ethicon). The pups were isolated, kept warm, and closely monitored for a minimum of 2 hours prior to returning them to their cage.

EXAMPLE 6
Monitoring of Diarrhea Induction.

Diarrhea induction by the NSP4 protein and peptides was carefully monitored for 24 hours following the inoculations. Each pup was examined every 1–2 hr for the first 8 hr and at 24 hr post inoculation by gently pressing on the abdomen. Diarrhea was noted and scored from 1 to 4 with a score of 1 reflecting unusually soft, loose, yellow stool, and a score of 4 being completely liquid stool. A score of 2 (mucous with liquid stool, some loose but solid stool) and above was considered diarrhea. A score of 1 was noted, but was not considered as diarrhea. The scoring was done by a single person and the pups were coded during analysis of diarrhea. Other symptoms monitored included lethargy, coldness to the touch, and ruffled coats in older animals.

EXAMPLE 7
Analysis of Chloride Secretion Reonsiveness to NSP4 114–135 in the Intestinal Mucosa of Mice.

Unstripped intestinal mucosal sheets from 19–22 and 35 day old mice were analyzed for chloride secretory responsiveness to NSP4 114–135. Short-circuit currents ($I_{ac}$) were measured across unstripped intestinal mucosal sheets from 19–22 and 35 day old CD1 mice using an automatic voltage clamp (Bioengineering, Univ. of Iowa) as described previously (30). The mid-ileum of the mouse intestines was utilized. The unstripped mucosal sheets taken from the intestine were placed into modified Using chambers with 0.12 cm$^2$ apertures (machine shope, UTHSC) and transepithelial potential ($V_t$) was registered by 3 M KCl agar bridges connected to balanced calomel half-cells. The transepithelial current required to clamp $V_t$ to 0 was passed through Ag—AgCl electrodes connected to the 3 M KCl bridges. All experiments were performed at 37° C. in bicarbonate Ringers solution gassed with 95% $O_2$-5% $CO_2$ by airlift circulators as previously described (same as above). The mucosal bath contained sodium-free (N-methyl-D-glutamine) substituted Ringers to minimize the effects on $I_{ac}$ of cAMP stimulated electrogenic Na$^+$/glucose co-transport across the small bowel (31). Following temperature and ionic equilibration, basal $I_{ac}$ measurements were taken and intestinal mucosal sheets were challenged with cross-linked peptide (either NSP4 114–135, NSP4 2–22, or mNSP4 131K), the calcium-elevating agonist carbachol (Cch), or the cAMP-agonist forskolin (FSK). Bumetamide sensitivity was tested and confirmed the chloride secretory response.

Results

EXAMPLE 8
NSP4 Protein Induces Age-dependent Diarrhea in Mice.

Whether administration was IP or intraileal (IL), diarrhea was observed within 1 to 4 hr post inoculation, typically continued for up to 8 hr, but occasionally persisted for 24 hr. Purified NSP4 (0.1–5 nmol) was administered by the IP route to 6–7 and 8–9 day old CD1 pups. In 6–7 day old CD1 pups, IP administration of 0.1 nmol of NSP4 induced diarrhea in 60% of the mice, whereas no disease was induced in 8–9 day old mice with the same concentration of protein (FIG. 1A). IP administration of 1 nmol of NSP4 resulted in 100% of the 6–7 day pups with diarrhea, and 60% of the 8–9 day old mice with disease. A larger dose of 5 nmol of NSP4 induced diarrhea in 90% of the older (8–9 day) mice. Additional clinical symptoms included lethargy and coldness to the touch, which were observed in the majority of treated animals with diarrhea of all ages. The induction of diarrhea by NSP4 was shown to be specific for this protein as administration of the same volume of buffer or VP6 had no effect.

IL administration of 0.5 nmol of purified NSP4 protein resulted in disease in 100% of the CD1 pups (8–9 day old mice) within the first 2 hr post inoculation, whereas no diarrhea was observed in 17–18 day old pups (Table 2, FIG. 1).

Thus, the response to NSP4 was age- and dose-dependent in CD1 pups. In addition, the induction of diarrhea by NSP4 was specific, as administration of the same concentration of purified rotavirus VP6 or the same volume of buffer had no effect (FIG. 1). The effect of IP and IL delivery of NSP4 protein in mice is the same. Intramuscular (IM) inoculation of 1 nmol of purified NSP4 produced no ill effects (data not shown). Subcutaneous and oral administration of NSP4 also produces no ill effects (data not shown).

Additional data showing a dose response in 6–7 day old CD1 pups is presented in FIG. 1B. The amount of peptide administered is shown in nanomoles and micrograms. 0.04–1.0 nmols (1–25 µg) of purified NSP4 was administered to 6–7 day old CD-1 pups by the IP route. A correlation between increasing incidence of diarrhea and increasing dose was seen (FIG. 1B) over the range tested. The highest tested dose (1.0 nmol=25 µg) induced diarrhea in all mice tested (10 of 10).

EXAMPLE 9
NSP4 114–135 Peptide Induces Diarrhea in Mice.

The NSP4 114–135 peptide has an AS of 35, is localized in the cytoplasmic domain of NSP4, and mobilizes intracellular calcium in eukaryotic cells (15, 16).

Following IP administration of 0.1 to 50 nmol of the NSP4 114–135 peptide, a similar disease response was noted in 6–7 day old CD1 outbred pups with 30–40% diarrhea induction (FIG. 2A). The percentage of CD1 pups with diarrhea increased to 60–70% following the IP delivery of 100–400 nmol of NSP4 114–135 and 89% of pups had diarrhea following administration of a dose of 500 nmol of peptide. Induction of disease in 100% of the CD1 pups was not achieved; doses exceeding 500 nmol were not administered since the volume of each dose was limited to 50µl . These data indicate the disease response in CD1 mice can be divided into three groups based on the dose of the NSP4 114–135 peptide, 1) less than and equal to 50 nmol (1 mM) resulting in 30–40% of the animals with disease, 2) 100–400 nmol (2–8 mM) yielding disease in 60–70% of the animals, and 3) 500 nmol and (10 mM) above inducing diarrhea in at least 89% of the young mice.

Figure 2B:
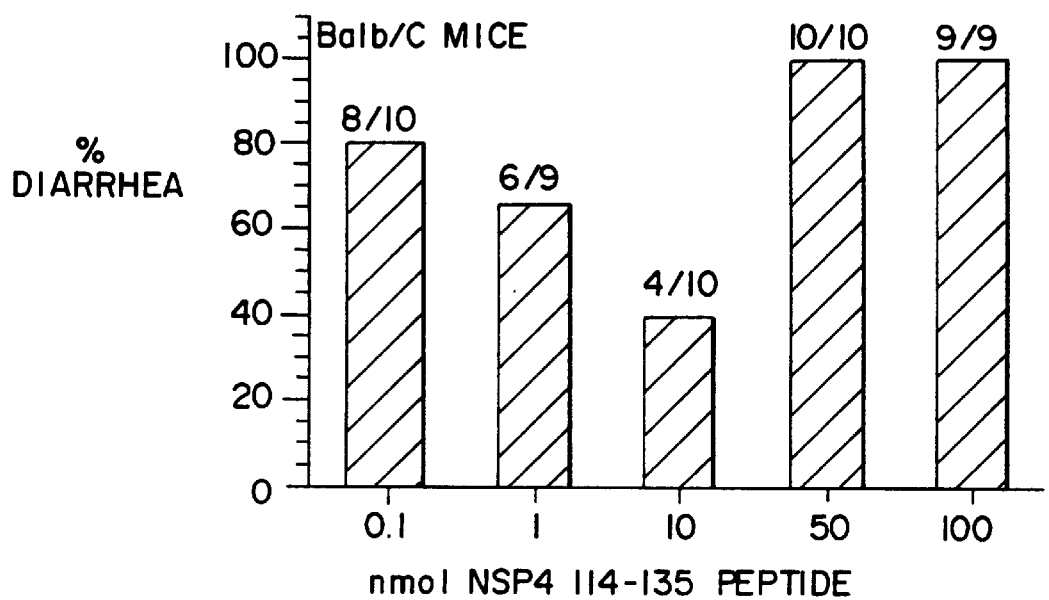

Diarrhea was induced in 100% of the 6–7 day old Balb/C pups with lower concentrations (only 50 nmol) of peptide (FIG. 2B), and diarrhea was observed in 80% of the Balb/C mice given 0.1 nmol (2µM) of NSP4 114–135. Hence the Balb/C pups appeared more sensitive to the effects of NSP4 114–135.

Taken together, doses exceeding 50 nmol (1 mM) of NSP4 114–135 peptide were sufficient to induce diarrhea in the majority of young mice when administered by the IP route. The diarrhea was observed within 1 to 4 hr post inoculation and typically continued for up to 8 hr, but occasionally was present for 24 hr. The severity of diarrhea typically increased with time. That is, a mouse with a diarrhea score of 1 in the first hr post inoculation would have a diarrhea score of 4 in the next hr. Various degrees of lethargy were noted following the administration of peptide and this was most pronounced at 3 to 4 hr post inoculation. The lethargy was accompanied by the pups being cold to the touch and was age-dependent. The severity of the induced diarrhea was greater in the Balb/C pups. No symptoms were noted with control peptides (NSP4 2–22, NV C-terminus) or PBS administered to the same age and species of mice.

EXAMPLE 10

NSP4 120–147 Peptide Induces Diarrhea in Mice.

A peptide corresponding to amino acid residues 120–147 of NSP4 was prepared and tested in 5–7 day old pups. When a dose of 100 nmols was administered, all (5 of 5) animals exhibited severe diarrhea. A dose of 5 nmols induced diarrhea in 7 out of 8 animals (88%). This demonstrates that other peptides derived from NSP4 can be prepared and screened to find the peptide with the highest activity. It is well within the ability of one of ordinary skill in the art to synthesize and screen a library of overlapping peptides that represents the entire sequence of the NSP4 protein in order to locate peptides with biological activity. One skilled in the art can readily appreciate that both the length of the peptides, and the number of residues that overlap in adjacent peptides, can be varied at the discretion of the practitioner without deviating from the spirit of the present invention.

EXAMPLE 11

Diarrhea induction in CD1 and Balb/C Mice by Cross-linked NSP4 114–135.

The NSP4 114–135 peptide was cross-linked to itself by glutaraldehyde and administered to young mouse pups by the IP route to determine if the diarrhea induction was affected by structure or oligomerization. Diarrhea was induced in the majority of the CD1 pups at a lower dose of NSP4 114–135 when the peptide was cross-linked to itself when compared to the peptide alone (FIG. 4). One nmol of cross-linked peptide induced diarrhea in 80% of the CD1 pups which increased to 90% with 250 nmol of cross-linked NSP4 114–135. As illustrated in FIG. 3, doses at or above 1 nmol (20 µM) of cross-linked peptide were sufficient to elicit a response in the majority of the CD1 pups. Increasing the dose above 1 nmol of cross-linked NSP4 114–135 had little effect, indicating the diarrheal response could not be increased with increased amounts of synthetic peptide, or that the response, once stimulated, could be saturated or additional stimulation had no effect.

Similar to the response in CD1 mice, diarrhea induction in 100% of the Balb/C pups was achieved with a lower dose (10 nmol, 200 µM) of cross-linked peptide when compared to the peptide alone (FIG. 4). In addition, the lethargy and coldness to the touch were more severe and lasted longer in animals that received the cross-linked peptide. Cross-linked NSP4 2–22 and NV C-terminus peptides were administered as controls and did not induce symptoms in young mice.

Induction of disease at a lower dose and with greater severity with the IP administration of cross-linked NSP4 114–135 suggests that cross-linking either stabilizes the peptide, oligomerizes the peptide, or results in a conformation more closely resembling the native protein. These data suggest structure may be important for disease induction.

EXAMPLE 12

Cross-linked NSP4 114–135 Peptide also Induces Diarrhea in Young Rats.

Figure 3A:
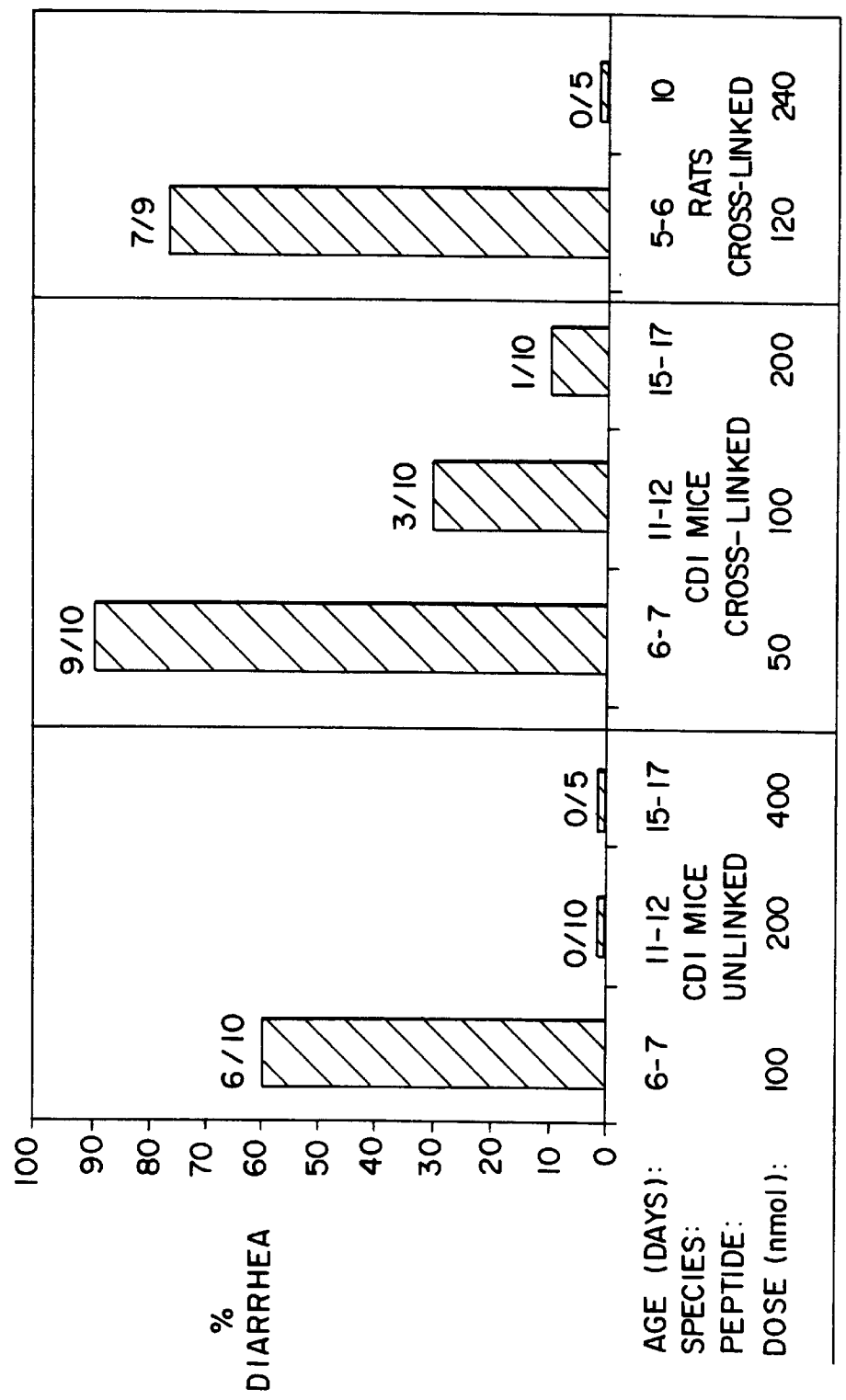

The NSP4 114–135 peptide was tested in a second species, the Sprague-Dawley rat to determine whether the disease response induced by this peptide was only effective in young mice. IP inoculation of 100–250 nmol of cross-linked peptide induced diarrhea in 78% of young (6 days) rat pups and in none of the older (10 day) rat pups (FIG. 3A). No disease was observed in the same age rodents administered control peptides. The response in rats was slower than that observed in mice, taking from 6 to 12 hr before the onset of diarrhea was noted, compared to 2 to 4 hours post inoculation for the mice, and required a higher concentration of peptide to observe disease. However, the induced diarrhea and lethargy in the young rats frequently persisted for up to 48 hr. These differences may reflect the difference in size and intestinal transit time between the rat and mouse or species (genetic) variation.

EXAMPLE 13

IL Delivery of NSP4 Peptide.

Figure 3B:
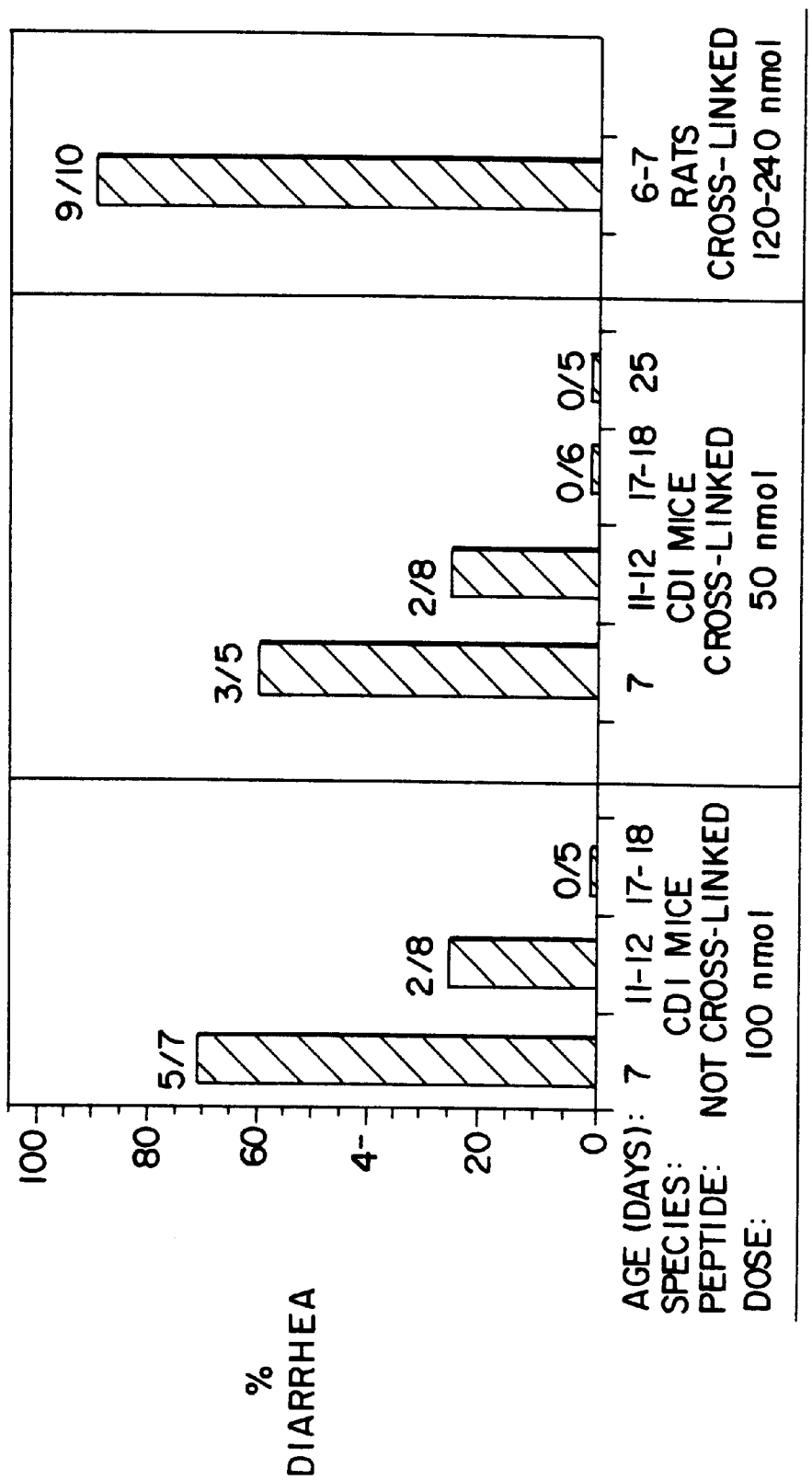

IL administration of 120–240 nmol of cross-linked NSP4 114–135 induced diarrhea in 90% of young (6–7 days) rat pups. Analogous to the response of young rats following the IP administration of cross-linked peptide, the onset of diarrhea was slower than that seen in the mice, taking from 6 to 12 hr, but lasted for a greater length of time (up to 48 hr). The surgical introduction of 10 nmol (200 µM) of cross-clinked peptide induced diarrhea in 100% of the young (8–9 days) Balb/C pups, identical to the induction of diarrhea following IP delivery (Table 2). The age-dependence of the diarrhea response noted with the IP administration of cross-linked NSP4 114–135 was maintained with the IL administration of cross-linked peptide. Only one-third of the 11–12 day old Balb/C mice had diarrhea when administered 10 nmol of cross-linked peptide by the IL route, and none of the 15–17 day animals had diarrhea. In addition, older CD1 mice (11–12 and 25 days) had no ill effects from the IL delivery of 50–200 nmol (1–4 mM) of cross-linked peptide (FIG. 3B, Table 2). An equal concentration of cross-linked NSP4 2–22 peptide or an equal volume of PBS, when surgically introduced in both young and older rodents, had no ill effects (data not shown).

Hence, the effect of IP and IL delivery of NSP4 peptide in rodents was equivalent.

EXAMPLE 14
Diarrhea Induction is Age Dependent.

Since rotavirus-induced diarrhea is age-dependent, we tested this parameter with the peptide. Between 100 and 300 nmol of NSP4 114–135 peptide, alone or cross-linked, was administered by the IP route to different age outbred mice and rats. Diarrhea was observed in the young mice within 2 to 4 hr post inoculation, whereas reduced or no symptoms were seen in older (11–12 or 15–17 days) animals (FIG. 3). With IP administration of peptide alone, disease was induced in 60% of the 6–7 day old CD1 pups with no symptoms noted in the 11–12 and 15–17 day old mice. IP administration of cross-linked peptide resulted in 90% diarrhea induction in 6–7 day old CD1 pups, 30% disease in 11–12 day old pups, and only 10% disease in 15–17 day old mice.

A comparable age dependence was observed with the Sprague-Dawley rats when cross-linked peptide was administered by the IP route. Diarrhea was detected 6 to 12 hr post inoculation in 78% of the young (5–6 day) rats while no disease was seen in the 10 day old rats given a similar dose of cross-linked peptide (FIG. 3). Thus an age dependence, similar to what is seen in a natural infection, is seen with the NSP4 114–135 peptide.

EXAMPLE 15
Induction of Diarrhea is Dose Dependent

To determine if the response to the NSP4 114–135 peptide was dose-dependent, 0.1–500 nmol of peptide were administered IP to 84 CD1 pups (6–7 days old; FIG. 2). The disease response to the NSP4 114–135 peptide was dose-dependent ($\chi^2_{trend}$=9.98, p=0.0016) with a DD$_{50}$ (50% diarrheal dose) of 79 nmol (10).

EXAMPLE 16
Specificity of the Diarrhea Response to Peptide NSP4 114–135.

Specificity of the diarrhea induction by the NSP4 114–135 peptide was confirmed by the administration of a panel of control peptides to young mouse pups (Tables 1 and 3).

Mutant peptide mNSP4 131K, in which the tyrosine at position 131 of NSP4 114–135 is replace with a lysine did not induce diarrhea (0/11), indicating the importance of this tyrosine residue in the induction of diarrhea. Neither did NSP4 2–22 or NV 464–483 cause diarrhea, 0/11 and 0/10, respectively. NSP4 90–123, which overlaps the 114–135 peptide by 9 residues, induced diarrhea in only 20% (2/10) of the mice tested (Table 3). The percentage of diarrhea induction increased to 50% when the NSP4 90–123 peptide was crosslinked. Cross-linked mutant (m)NSP4 131k peptide induced diarrhea in 2 of 10 mice, while cross-linked NV 464–483 did not cause disease. Thus, the response to peptide alone appears to be directed to a region of NSP4 inclusive of residues 114–135.

EXAMPLE 17
Administration of Peptide NSP4 114–135 Results in Stunted Growth.

Figure 6:
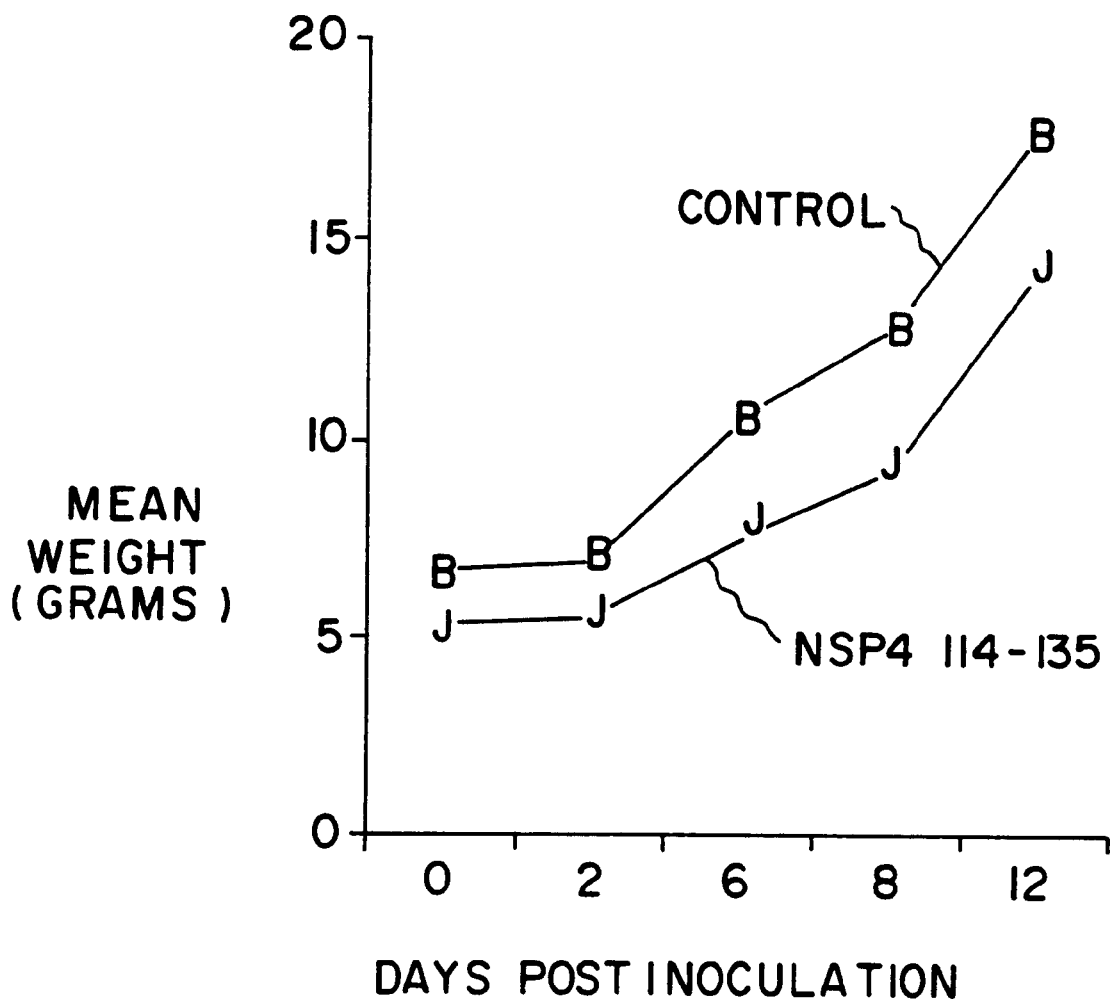

Animals given peptide three times per day for two days showed a rapid onset of severe diarrhea followed by stunted growth. The weight of these animals was 20–30% lower for three weeks after administration of peptide, (FIG. 6). These results mimic characteristics of rotavirus disease in animals and children, including the fact that both may show decreased growth rates after multiple infections.

EXAMPLE 18
Antiserum to NSP4 114–135 Peptide Blocks Induction of Diarrhea

We also evaluated whether antiserum made to the NSP4 114–135 peptide was able to block the induction of diarrhea (32). In the absence of antibody, IP delivery of 50–100 nmol of NSP4 114–135 peptide induced diarrhea in 67% of the mice. IP inoculation of NSP4 114–135 peptide-specific antiserum 5 mins prior to IP delivery of peptide (50–100 nmol) resulted in a 90% reduction of disease. IP administration of normal rabbit serum prior to peptide did not block the diarrhea.

EXAMPLE 19
NSP4 Antibodies Protect Against Virus-induced Disease.

The potential of NSP4 antibodies to protect against virus-induced disease was tested by challenging pups, born to dams which were immunized with the NSP4 114–135 peptide or a control peptide, with a high dose of infectious SA11 virus (33), FIG. 5, left hand side. Diarrheal disease in pups born to dams immunized with the NSP4 114–135 peptide was significantly (Fisher's exact test) reduced in severity, duration, and in the number of pups with diarrhea (Table 5). The NSP4 2–22 peptide was used as a control peptide, as it does not induce diarrhea in pups.

In another experiment, young mouse pups were infected with SA11 virus, and NSP4 antiserum or control antiserum was orally administered every 4–6 hours for 60 hr, FIG. 5, right hand side. The pups administered NSP4-specific antibody had significantly reduced diarrheal disease compared to animals given no treatment, rabbit pre-immune serum or normal rabbit serum (NRS) (33), (Table 6). These data show the potential of NSP4 antibodies to block rotavirus-induced disease.

EXAMPLE 20
Electrophysiological Analyses

The above data suggest NSP4 causes diarrhea by acting as an enterotoxin. Because enterotoxins stimulate net secretion in ligated intestinal segments without histological alterations, or stimulate secretion in Using chambers, the effects of the peptide, and known $Ca^{2+}$—and cAMP-elevating agonists were tested on unstripped mouse intestinal mucosal sheets in modified Using chambers (14). Addition of forskolin (FSK, cAMP agonist) and carbachol (Cch, cholinergic agonist which mobilizes $Ca^{2+}$) to normal mouse ileal mucosa resulted in measurable elevations in $Cl^-$ secretory short circuit current ($I_{ac}$ Table 4). Addition of either 5 $\mu$M of NSP4 114–135 peptide (cross-linked to itself for enhanced stability) or 5 $\mu$M of Cch to mucosal sheets of 19–22 day old CD1 mice induced small (3 or 9 $\mu$A/cm$^2$, respectively) and transient (1–2 min) increases in $I_{ac}$. When the mucosal sheets were exposed to 5 $\mu$M of the cAMP-mobilizing agonist, FSK, larger increases in $I_{ac}$ (44 $\mu$A/cm$^2$) were elicited that reached sustained levels within 2–3 min. After FSK pretreatment, challenge of the mucosa with either peptide or Cch resulted in much larger increases in mucosal $I_{ac}$ (64 or 63 $\mu$A/cm$^2$, respectively) both the peptide and Cch potentiated the response to FSK. All of the responses to agonists were sensitive to bumetamide and treatment of ileal mucosal sheets with cross-linked control NSP4 2–22 peptide did not induce a response. Addition of Cch to 19–22 day old mouse mucosal sheets which had been pretreated with peptide alone, or peptide in combination with FSK, had minimal or no additional effect on $I_{ac}$. This subsequent loss of sensitivity to the $Ca^{2+}$-elevating agonist (Cch) after peptide pretreatment suggests that the NSP4 peptide increases $I_{ac}$ through changes in intracellular $Ca^{2+}$ ([$Ca^{2+}$]i).

Addition of Cch to mucosa from a 35 day old mouse again elicited a small (14 $\mu$A/cm$^2$) and transient (1–2 min) response that potentiated the effect of FSK (64 $\mu$A/cm$^2$), whereas there was no or minimal increase in I$_{ac}$ when the NSP4 114–135 peptide was added alone or with FSK to the 35 day old mouse mucosal sheets (Table 4).

The electrophysiological responses from 19 day old mice initially seem paradoxical to the biological data since measurable secretion was not observed as diarrhea in this age animal. Diarrhea likely was not seen in these older animals because of fluid reabsorption by the colon. This hypothesis was tested by IL administration of 200 nmol of NSP4 114–135 or control peptide to 19 day old pups. At 4 hrs post inoculation, the mice were sacrificed and the intestines were tied off, removed, weighed, and the length measured. The pups given NSP4 114–135 peptide showed significant fluid accumulation when compared to the control pups although no diarrhea was seen in any animals.

We anticipate that younger mice would show a greater increase in I$_{ac}$ than that seen in the 19 day old mucosa. However, intestinal mucosa from younger mice (<19 days) could not be mounted efficiently into the Using chambers due to their small size; such experiments in very young mice will require the development of new methods to measure Cl$^-$ secretion in vitro. Nonetheless, the NSP4 114–135 peptide did not augment secretion in 35 day old mice, correlating the age-dependence seen in vivo.

EXAMPLE 21
Model for Rotavirus-induced Diarrheal Disease.

Based on our results on NSP4-induced diarrhea in mice and rats, we propose a model in which two intestinal receptors are required for symptomatic rotavirus infection. One receptor binds rotavirus particles resulting in virus entry and gene expression, but not necessarily disease, whereas the second receptor is NSP4-specific. NSP4 expressed in infected cells would be released into the lumen and interact with the second receptor on adjacent cells. This interaction would trigger a signal transduction pathway, thereby increasing [Ca$^{2+}$]$_i$ levels and augmenting endogenous intestinal secretory pathways. Using a newly established ELISA which is sensitive enough to detect 31.3 ng or 0.02 nmol of NSP4, we have detected NSP4 in the diarrheal stools of rotavirus infected mice at concentrations necessary to induce disease. NSP4 was not present in stools from animals without diarrhea.

This model fits available data on rotavirus-induced diarrhea. In young mice, homologous and heterologous rotaviruses cause diarrheal disease. For example, in young mice infected with the simian virus, SA11, infectious virus is not produced, histopathologic blunting of the villi is not observed, but diarrhea is induced (34). In other animals, diarrhea is seen prior to histologic changes (12). Adult mice are readily infected by murine rotaviruses, but do not display diarrhea or other symptoms (35). However, virus can be isolated from fecal samples and virus replication can be demonstrated in intestinal cells from adult animals (32).

According to this model, the intestines of young mice possess a NSP4-specific receptor that decreases in number or structure or activity as the mouse ages, and interactions with this receptor stimulate Cl$^-$ secretion resulting in the observed diarrheal disease. Our model predicts that the binding activities or concentration of NSP4 receptors is significantly reduced in adult animals such that the colon can accommodate the increase in fluid secretion. The adult mouse can replicate and excrete virus, but no disease is observed. That is, while the receptor for rotavirus infection is maintained with age, allowing the adult mouse to replicate and excrete virus, the NSP4 receptor is not maintained with developmental aging, so disease is not observed.

Further support for our model comes from our observation that NSP4 causes diarrhea in young rats. No group A rotavirus has been shown to infect rats, suggesting that these animals lack the receptor for virus infection. However, the induction of diarrhea with NSP4 indicates the receptor for this protein is present and can be stimulated by NSP4 resulting in an increase in intracellular calcium levels and disease.

These data collectively demonstrate that NSP4 is an enterotoxin: NSP4 and NSP4 114–135 and 120–147 peptides induce diarrhea in two rodent models; diarrhea induction is specific, age- and dose-dependent; and electrophysiologic analyses in Ussing chambers reveal that NSP4 stimulates Cl$^-$ secretion by a Ca$^{2+}$-dependent pathway in young mouse intestinal mucosa. NSP4 interacts with an age-dependent intestinal receptor, triggers a signal transduction pathway, and increases [Ca$^{2+}$]$_i$ resulting in Cl$^-$ secretion or diarrhea.

EXAMPLE 22
Live Rotavirus and NSP4 Cause Diarrhea in CFTR Knock-out Mice.

Cystic Fibrosis is caused by a defect in the gene that codes for the cAMP-activated chloride channel called CFTR. As a result of the defect, the CFTR channel is defective and chloride secretion—and hence water secretion—is greatly diminished. Without sufficient secretion of water, membranes accumulate excessive amounts of mucous and eventually become obstructed. We tested our theory that NSP4 stimulation of chloride secretion through the alternate calcium-dependant chloride channel might compensate for the deficient secretion in Cystic Fibrosis patients. We administered peptide or virus to 5–7 day old CFTR knock-out mice—mice homozygous for a mutation that disables the CFTR coding region—and got diarrhea in 100% of the cases for virus and cross-linked peptide or in 80% of the animals given 100 nmoles of non-crosslinked NSP4 114–135 peptide. This demonstrates that NSP4 stimulation of chloride secretion through the Ca$^{2+}$-dependent channel can compensate for the lack of secretion through the defective cAMP-dependent CFTR channel.

EXAMPLE 23
HIV gp120 Causes Diarrhea in Mice.

Human immunodeficiency virus (HIV) is associated with wasting or Slim disease. To determine whether the HIV glycoprotein 120 (gp120) is an enterotoxin, 6–7 day old Balb/C mouse pups were inoculated with purified gp120. Diarrhea was observed in 100% of the animals. Other proteins of HIV or other retrovirus or other proteins of other viruses may be found to have similar functional activity—i.e., to directly induce diarrhea.

EXAMPLE 24
Identification of Small Molecule Inhibitors of NSP4/Receptor Interaction.

The above data demonstrate that effective treatment of rotavirus-induced diarrhea can be accomplished through inhibition of NSP4's interaction with its receptor. Identification of small molecule inhibitors of NSP4 is well within the ability of the ordinary practitioner according to known techniques. Small molecule inhibitors are known in the art to refer to any ligand which can bind to a target molecule with sufficient affinity to inhibit the target molecule's activity. Libraries of small molecules, such as random peptide libraries, random oligonucleotide libraries, and pharmaceutical drug libraries, are available either according to known techniques or commercially, and may be quickly and easily screened against a purified target molecule for small molecules that bind with high affinity to a target molecule. Examples include the "FliTrx Peptide Library," (Invitrogen) and the SELEX technology.

EXAMPLE 25
Construction of Attenuated Rotavirus Strains by Incorporation of a Selected NSP4 Amino Acid Sequence.

The sequence of gene 10, the gene encoding NSP4, was determined for a pair of virulent and tissue culture attenuated porcine rotavirus strains. Double stranded RNAs were extracted from an intestinal homogenate from a piglet infected with a virulent strain of porcine rotavirus (OSU-v) and from a piglet infected with a tissue culture attenuated OSU virus (OSU-a). Gene 10 from the dsRNAs was amplified by RT/PCR using primers from the SA11 gene 10 sequence. cDNAs from these two strains were cloned and sequenced. Comparisons of the gene 10 sequences of these two strains and other rotavirus strains have suggested that the amino acid sequence between amino acids 131 to 140 are important in pathogenesis. The amino acid sequence of the NSP4 protein from the attenuated strain (OSU-a) (SEQ ID NO. 1) was compared to that of the virulent strain (OSU-v) (SEQ ID NO. 8) and the results are presented in FIG. 7. The positions at which the two sequences differ are shown in bold. Mice infected with virulent virus develop diarrhea while those infected with attenuated virus do not.

Gene 10 encoding NSP4 protein from each of these two strains has been cloned and expressed in a baculovirus expression system and purified. The purified NSP4 proteins were tested for their ability to induce diarrhea in mouse pups. The NSP4 protein from the virulent strain causes increased intracellular calcium concentration and induced diarrhea while that of the attenuated strain did not. These results indicate that avirulence is associated with mutations in gene 10 and indicate that certain amino acid positions of the NSP4 protein are critical for diarrhea induction. The identification of critical residues makes it a routine matter for one skilled in the art to determine whether a given rotavirus is likely to cause diarrhea by comparing the amino acid sequence of the NSP4 protein to known sequences. In addition, the identification of NSP4 sequences that correlate to an attenuated phenotype makes it a routine matter to construct attenuated reassortment viruses that include such an NSP4 sequence, using techniques that are well known to those skilled in the art. This permits the construction of rotaviruses for use as vaccines that retain the antigenicity of the virulent strain yet display an attenuated phenotype as a result of the incorporation into the genome of the virus a nucleic acid coding for an NSP4 protein having a selected sequence.

EXAMPLE 26

Preparation and Use of an NSP4 Toxoid.

Vaccines comprising NSP4 in the form of a toxoid may be prepared from purified NSP4 protein. The purified protein can be chemically treated, using known techniques, to inactivate the biological activity of the NSP4 protein while retaining the immunogenicity. For example, the purified protein may be treated with a 10% solution of formaldehyde at about 37 degrees for about an hour. One skilled in the art will recognize that other equivalent protocols to produce a toxoid may be employed without deviating from the spirit of the invention. After chemical treatment the toxoid will typically be washed with buffer, for example phosphate buffered saline or the like, and formulated into a vaccine. The toxoid may be in solid form such as adsorbed to alum or the like. Alternatively, the toxoid may be in solution in any pharmaceutically acceptable liquid. The toxoid may be administered as a vaccine in the absence of adjuvant. A vaccine formulated with the toxoid may include adjuvants including but not limited to alum, Freund's complete and incomplete adjuvants, Ribi's adjuvant, bacterial and mycobacterial cell wall components and derivatives thereof, liposomes and any other adjuvant formulation known in the art. Vaccines thus formulated may be administered using parenteral or mucosal routes such as by intraperitoneal, intranasal, intragastric, subcutaneous, intramuscular, or rectal application.

EXAMPLE 27

Characterization of the Receptor for NSP4.

The human intestinal cell line HT29 was assayed for sensitivity to NSP4. In response to purified NSP4, these cells showed an increase in intracellular calcium levels. When these cells are pre-treated with trypsin, the response is ablated. The binding of radiolabelled NSP4 protein to responsive cells is dose-dependent and saturable as would be expected for a receptor dependent phenomenon. Taken together, these two results demonstrate that NSP4 binds to a protein receptor. Recent tests with respiratory epithelial cells have demonstrated that these cells do not respond to NSP4 and do not bind radiolabelled NSP4 protein. It is well within the ability of one of ordinary skill in the art to identify the receptor by expression cloning in these nonresponsive cells that do not bind NSP4. The mRNA from a responsive cell can be isolated using standard techniques and reverse transcribed into cDNA. This cDNA can then be inserted into a vector and then used to transform the nonresponsive cell line. Alternatively, the genomic DNA from the responsive cells may be inserted into a vector and used to transform the nonresponsive cell line. The transformed cells will be screened for the expression of the receptor using routine techniques, for example, by screening for cells capable of binding radiolabelled NSP4. Cells that express the receptor will be isolated.

The presence compounds that inhibit the G-protein/phospholipase C signal transduction pathway also abrogate the intracellular calcium increase seen in response to NSP4, suggesting the involvement of this pathway in the observed response. One skilled in the art can envision the use of inhibitors specific for the G-protein/phospholipase C pathway as therapeutic agents for the treatment of NSP4 induced diarrhea. The use of such compounds is within the spirit of the present invention.

CITATIONS

1. A. Z. Kapikian and R. M. Chanock, in *Virology*, B. N. Fields and D. M. Knipe, Eds. (Raven Press, New York, 1996) chap. 55.
2. J. Halvorsrud and I. Orstavik, *Scand. J. Infect. Dis.* 12, 161 (1980).
3. H. Holzel, D. W. Cubitt, D. A. McSwiggan, P. J. Sanderson, J. Church, *J. Infect. Dis.* 2, 33 (1980).
4. M. K. Estes, E. L. Palmer, J. F. Obijeski, *Curr. Top. Microbiol. Immunol.* 105, 123 (1983); H. B. Greenberg, H. F. Clark, P. A. Offit, ibid. 185, 255 (1994).
5. R. f. Ramig, *Microbial Pathogenesis* 4, 189 (1988). J. L. Wolf, G. Cukor, N. R. Ballcklow, R. Dambrauskas, J. S. Trier, *Infec. Immun.* 33, 565 (1981). Riepenhoff-Talty, P. C. Lee, P. J. Carmody, H. J. Barrett, P. L. Ogra, *Proc. Soc. Exp. Biol. Med.* 170, 146 (1982).
6. Riepenhoff-Talty, P. C. Lee, P. J. Carmody, H. J. Barrett, P. L. Ogra, *Proc. Soc. Exp. Biol. Med.* 170, 146 (1982).

7. J. L. Wolf, G. Cukor, N. R. Ballcklow, R. Dambrauskas, J. S. Trier, *Infec. Immun.* 33, 565 (1981)
8. H. B. Greenberg, H. F. Clark, P. A. Offit, *Curr. Top. Microbiol. Immunol.* 185, 255.
9. D. Y. Graham, J. W. Sackman, M. K. Estes, *Dig. Dis. Sci.* 29, 1028 (1984).
10. J. Collins, et al., *J. Pediatr. Gastroenterol. Nutr.* 7, 264 (1988).
11. M. P. Osborne et al., *J. Pediatr. Gastroenterol. Nutr.* 7, 236 (1988).
12. K. W. Theil, E. Bohl, R. Cross, E. Kohler, A. Agnes, *Am. J. Vet. Res.* 39, 213 (1978); J. P. McAdaragh et al., ibid 41, 1572 (1980); L. J. Saif, L. A. Ward, L. Yuan, B. I. Rosen, T. L. To, in *Proceedings of the Sapparo International Symposiums on Viral Gastroentritis*, S. Chiba, S. Nakata, and M. K. Estes, Eds. (Arch. of Virol. Special Issue) in press; C. A. Mebus, *Am. J. Dig. Dis.* 21, 592 (1976).
13. M. N. Burges, et al., *Infect. Immunol.* 221, 526 (1978); R. A. Giannella, *Ann. Rev. Med.* 32,341 (1981); W. J. Krause, R. H. Freeman, L. R. Forte, *Cell and Tissue Res.* 260, 387 (1990).
14. R. A. Giannella, M. Luttrell, M. Thompson, *Am. J. Phys.* 245, G492 (1983); M. G. Currie et al., *Proc. Natl. Acad. Science USA* 89, 947 (1992); M. Field, L. H. Graf, W. J. Larid, P. L. Smith, *Proc. Natl. Acad. Science USA* 75, 2800 1978); L. R. Forte, et al., *Am. J. Phys.* 263, C607 (1992).
15. P. Tian, Y. Hu, W. P. Schilling, D. A. Lindsay, J. Eiden, M. K. Estes, *J. Virol.* 68, 51 (1994).
16. P. Tian, M. K. Estes, Y. Hu., J. M. Ball, C. Q.-Y. Zeng, W. P. Schilling, *J. Virol.* 69, 576 (1995).
17. J. Levin and F. B. Bang, *Throm. Diath. Haemorrh.* 19, 186 (1968); T. J. Novitsky, Oceanus 27, 13 (1984).
18. C. Q.-Y. Zeng, M. J. Wentz, J. Cohen, M. K. Estes, R. F. Ramig, *J. Virol.*, in press (1996).
19. J. M. R. Parker, D. Guo, R. S. Hodges, *Biochemistry* 25, 5425 (1986).
20. P. Y. Chou and G. D. Fassman, *Adv. in Enz.* 47, 45 (1978).
21. H. Margolit et al., *J. Immunol.* 138, 2213 (1987).
22. Dyson, et al., *J. Mol. Biol.* 201, 161 (1988). Dyson, et al., *J. Mol. Biol.* 201, 201 (1988). P. E. Wright, et al., *Biochemistry* 27, 7167 (1988). Dyson, et al., *Biophysical Chem.* 20,519 (1991). Dyson, et al. *Ann. Rev. Biophys. Biophysical Chem.* 17, 305 (1988). Dyson, et al., *FASEB J.* 9, 37 (1995). J. Yao, et al., *J. Mol. Biol.* 243, 736 (1994). Waltho, et al., *Biochemistry*, 32, 6337 (1993). Dyson, et al., *Biochemistry*, 31, 1458 (1992).
23. G. W. Both, L. J. Siegman, R. R. Bellamy, P. H. Atkinson, *J. Virol.* 48, 335 (1983).
24. X. Jiang, D. Y. Graham, P. Madore, T. Tanaka, M. K. Estes, *Science* 250, 1580 (1990).
25. L. A. Carpino and G. H. Han, *J. Org. Chem.* 37, 5748 (1970).
26. E. Kaiser, R. L. Colescott, C. D. Bosinger, P. I. Cook, *Anal. Biochem.* 34 595 (1970).
27. G. P. Johnson et al., *Anal. Chem.* 58, 1084 (1986).
28. Reichlin, *Methods in Enzym.* 70, 159 (1980).
29. J. M. Ball, N. L. Henry, R. C. Montelaro, J. J. Newman, *J. Immunol Methods* 171, 37 (1994).
30. C. L. Sears, R. L. Guerrant, J. B. Kaper, in *Infections of the Gastrointestinal Tract*, M. J. Blaser, P. D. Smith, J. I. Ravdin, H. B. Greenberg, R. L. Guerrant, Eds. (Raven Press, New York, 1995), chap. 44; A. P. Morris S. A. Cunningham, A. Tousson, D. J. Benos, R. A. Frizzell, *Am J. Physiol.* 266, C254 (1994).
31. B. R. Grubb, *Am. J. Physiol.* 268, G505 (1995).
32. L. M. Little and J. A. Shadduck, Infect. Immun. 38, 755 (1982); W. G. Starkey et al., *J. Gen. Virol.* 67, 2625 (1986).
33. Ball and Estes, manuscript in preparation.
34. R. F. Ramig, *Microbial Pathogenesis* 4, 189 (1988).
35. R. L. Ward, M. M. McNeal, J. F. Sheridan, *J. Virol.* 64, 5070 (1990); N. Feng, H. W. Burns, L. Bracy, H. B. Greenberg, J. Virol. 68, 7766 (1994); J. W. Burns, et al., *Virol.* 207, 143 (1995).

The invention disclosed herein is not considered to be limited by any statements made herein.

TABLE 1

| Peptide | Sequence[1] | AS[2] | Pt[3] | Mr[4] |
| --- | --- | --- | --- | --- |
| NSP4 114–135 | DKLTTREIEQVELLKRIYDKLT | 35 | 1.12 (YDKL) | 2705 |
| NSP4 2–22 | EKLTDLNYTLSVITLMNNTLH | 13.9 | 1.12 (TDLN) | 2434 |
| NSP4 90–123 | TKDEIEKQMDRVVKEMRRQLEMI<u>DKLTTREIEQ</u> | 70.6 | 1.11 (TKDE) | 4092 |
| NSP4 m131K | DKLTTREIEQVELLKRI(K)DKLT | 31.4 | 1.08 (KDKL) | 2669 |
| NV 464–483 | KTGRNLGEFKAYPDGFLTCV | 41.4 | 1.58 (YPDG) | 2204 |

[1]NSP4 sequence from rotavirus SA11 (Both et al., 1983). Norwalk virus (NV) sequence from Jiang et al., 1990. Underlined sequence is the region of the NSP4 2–22 peptide which overlaps with the NSP4 114–135 peptide. This substitution decreases the turn potential from 1.12 to 1.08. The mutated tyrosine to lysine residue is shown in bold and in parentheses.
[2]AS = amphipathic score. A block length of 11 was used with an AS of 4 considered significant (Margolit et al., 1987).
[3]Pt = turn potentials greater than 1.0 within the selected peptide based on the algorithm of Chou and Fasman (1974, 1978).
[4]Mr = Theoretical mass.

TABLE 2

Intraileal administration of NSP4 and NSP4 114–135.

| Species | Age (days) | Inoculum | Concentration (nmol) | Diarrhea |
|---|---|---|---|---|
| Sprague-Dawley rat | 6–7 | X-linked NSP 4 114–135 | 120–240 | 9/10 |
| Balb/C mice | 8–9 | X-linked NSP 4 114–135 | 10 | 6/6 |
| Balb/C mice | 11–12 | X-linked NSP 4 114–135 | 10 | 2/6 |
| Balb/C mice | 15–17 | X-linked NSP 4 114–135 | 10 | 0/6 |
| CD1 mice | 7 | X-linked NSP 4 114–135 | 50 | 3/5 |
| CD1 mice | 11–12 | X-linked NSP 4 114–135 | 50 | 2/8 |
| CD1 mice | 17–18 | X-linked NSP 4 114–135 | 50 | 0/6 |
| CD1 mice | 25 | X-linked NSP 4 114–135 | 50 | 0/5 |
| CD1 mice | 25 | X-linked NSP 4 114–135 | 100–200 | 0/8 |
| CD1 mice | 8–9 | NSP4 protein | 0.5 | 5/5 |

TABLE 3

Specificity of the Diarrheal Response:
Diarrhea Induction in CD1 Mice following IP Administration of 50–100 nmol Peptide

| Peptide | % Diarrhea | # responders/total # tested |
|---|---|---|
| NSP4 114–135 | 67 | 8/12 |
| antibody[a] + NSP4 114–135 | 10 | 1/10 |
| cross-linked NSP4 114–135 | 75 | 15/20 |
| mNSP4 131K[b] | 0 | 0/11 |
| cross-linked mNSP4 131K | 20 | 2/10 |
| NSP4 2–22 | 0 | 0/11 |
| cross-linked NSP4 2–22 | 0 | 0/17 |
| NSP4 90–123 | 20 | 2/10 |
| cross-linked NSP4 90–123 | 50 | 4/8 |
| NV 463–486 | 0 | 0/10 |
| cross-linked NV 463–486 | 0 | 0/9 |

[a]rabbit hyperimmune anti-NSP4 114–135 serum administered just prior to administration of the peptide
[b]single amino acid substitution at residue 131

TABLE 4

Electrophysiological Analyses of CD1 Mice Ileal Mucosa

| Agonist Treatment[a] | 19–22 Day Old Mice $\Delta I_{SC}$ ($\mu A/cm^2$)[b] | 35 Day Old Mice $\Delta I_{SC}$ ($\mu A/cm^2$)[b] |
|---|---|---|
| Forskolin (FSK), 5 $\mu M$ | 44 ± 0.7 (n = 8) | 41 ± 7 (n = 5) |
| Carbachol (Cch), 5 $\mu M$ | 9 ± 2 (n = 8) | 14 ± 4 (n = 5) |
| NSP4 114–135 peptide, 5 $\mu M$[c] | 3 ± 0.2 (n = 4) | 0.4 ± 0.4 (n = 4)[d] |
| FSK (5 $\mu M$) = Cch (5 $\mu M$) | 63 ± 10 (n = 5) | 64 ± 9 (n = 6) |
| FSK (5 $\mu M$) + NSP4 114–135 peptide (5 $\mu M$) | 64 ± 5 (n = 7) | 43 ± 9 (n = 5) |

[a]The mean resting conductance for the ileal mucosal sheets prior to agonist treatment was 10.4 ± 4.8 msemens (ms)/cm² (n = 32) for the 19–22 day old mice and 12.3 ± 3.8 ms/cm² (n = 25) for the 35 day old mice.
[b]The $\Delta I_{SC}$ was calculated by subtracting the stimulated $I_{SC}$ measurement from the $I_{SC}$ measured immediately before the addition of agonist. All agonist stimulated values were significantly different (p < 0.001, unpaired t-test).
[c]NSP4 114–135 peptide is active when added to either surface of the mucosa.
[d]For n = 3, there was no response with peptide; for n = 1, the response was 2 $\mu A/cm^2$

TABLE 5

Immunizaton with NSP4 114–135 peptide induces protective immunity from infectious rotavirus challenge Diarrhea Observed in Passively Immunized Pups[a]

| Peptide | % pups with diarrhea[b] total | 2 days | 3 days | Mean Diarrhea Score |
|---|---|---|---|---|
| NSP4 2–22 | 100% (16/16) | 63% (10/16) | 25% (4/16) | 3.5+ |
| NSP 4 114–135 | 42% (5–12) | 17% (2/12) | 0% (0/12) | 2.0+ |
| | *P = <0.001 | P = <0.025 | NS | |

*Fischer's Exact Test
[a]Pups born to dams immunized with NSP4 114–135 or control peptide were challenged with a high dose of infectious SA11 rotavirus and diarrheal disease was monitored.
[b]Significant protection against disease was seen in pups born to mothers immunized with NSP4 114–135 peptide.

TABLE 6

Protection from Rotavirus Severe Diarrhea (≧3+) after Administration of NSP4-specific Antibody

| Treatment | | Total # with Diarrhea | Onset of Diarrhea (hpi) | Illness at 71–77 hpi | Illness at 90–110 hpi |
|---|---|---|---|---|---|
| None | Exp. 1 | 7/7 (100%) | 27–28 (5/7 | 4/7 (57%) | 2/7 (29%) |
| | Exp. 2 | 10/10 (100%) | 22–23 6/10 | 4/10 (40%) | 3/10 (30%) |
| Rab pre immune | Exp. 1 | 8/8 (100%) | 27–28 5/8 | 4/8 (50%) | 0/8 (0%) |
| NRS | Exp. 2 | 13/13 (100%) | 22–24 3/14 | 2/13 (15%) | 0/13 (0%) |
| Rabbit anti-NSP4 | Exp. 1 | 5/10* (50%) | 27–28 3/10 | 1/8 (12%) | 0/8 (0%) |
| | Exp. 2 | 2/13* (15%) | 27–28 1/13 | 0/10 (0%) | 0/10 (0%) |
| Rabbit anti-NSP4 | Exp. 1 | ND | ND | ND | ND |
| anti-NSP4 114–135 peptide | Exp. 2 | 2/9* (22%) | 22–23 1/9 | 0/9 (0%) | 0/9 (0%) |

*Statistically significant compared to the pre immune or no treatment groups; Fischer's exact (2-tailed). ND = not done.

We claim:

1. A method of immunization against rotavirus infection or disease comprising administering to a subject a peptide NSP4 114–135 or a toxoid thereof.

2. A method for passive immunization against rotavirus infection or disease comprising administering to an expectant mother a peptide NSP4 120–147 or toxoid thereof.

3. A method of immunization against rotavirus infection or disease comprising administering to a subject a peptide NSP4 120–147 or a toxoid thereof.

4. A method for passive immunization against rotavirus infection or disease comprising administering to an expectant mother a peptide NSP4 114–135 or a toxoid thereof.

5. The method of claim 1 or 3, wherein said peptide or toxoid thereof is produced by a synthetic method.

6. The method of claim 1 or 3 wherein said peptide or toxoid thereof is produced by an expression vector.

* * * * *

SEQUENCE LISTING

<160> NUMBER OF SEQ ID NOS: 8

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 1

Asp Lys Leu Thr Thr Arg Glu Ile Glu Gln Val Glu Leu Leu Lys Arg
 1               5                  10                  15

Ile Tyr Asp Lys Leu Thr
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 2

Glu Lys Leu Thr Asp Leu Asn Tyr Thr Leu Ser Val Ile Thr Leu Met
 1               5                  10                  15

Asn Asn Thr Leu His
            20

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 3

Thr Lys Asp Glu Ile Glu Lys Gln Met Asp Arg Val Val Lys Glu Met
 1               5                  10                  15

Arg Arg Gln Leu Glu Met Ile Asp Lys Leu Thr Thr Arg Glu Ile Glu
            20                  25                  30

Gln

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 4

Asp Lys Leu Thr Thr Arg Glu Ile Glu Gln Val Glu Leu Leu Lys Arg
 1               5                  10                  15

Ile Lys Asp Lys Leu Thr
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 5

Asp Thr Gly Arg Asn Leu Gly Glu Phe Lys Ala Tyr Pro Asp Gly Phe
 1               5                  10                  15

Leu Thr Cys Val
            20

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      NSP4-specific control peptide

<400> SEQUENCE: 6

Glu Ile Glu Gln Val Glu Leu Leu Lys Arg Ile Tyr Asp Lys Leu Thr
 1               5                  10                  15

Val Gln Thr Thr Gly Glu Ile Asp Met Thr Lys Glu
            20                  25

<210> SEQ ID NO 7
<211> LENGTH: 175
<212> TYPE: PRT
<213> ORGANISM: Porcine rotavirus

<400> SEQUENCE: 7

Met Asp Lys Leu Ala Asp Leu Asn Tyr Thr Leu Ser Val Ile Thr Leu
 1               5                  10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Met Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Val Asp Arg Ile Ile Lys Glu Met Arg Arg Gln Leu Glu Met

-continued

```
                        100                 105                 110
Ile Asp Lys Leu Thr Thr Arg Glu Ile Glu Gln Val Glu Leu Leu Lys
            115                 120                 125

Arg Ile His Asp Lys Leu Ala Ala Arg Ser Val Asp Ala Ile Asp Met
        130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175

<210> SEQ ID NO 8
<211> LENGTH: 175
<212> TYPE: PRT
<213> ORGANISM: Porcine rotavirus

<400> SEQUENCE: 8

Met Asp Lys Leu Ala Asp Leu Asn Tyr Thr Leu Ser Val Ile Thr Leu
  1               5                  10                  15

Met Asn Asp Thr Leu His Ser Ile Ile Gln Asp Pro Gly Met Ala Tyr
             20                  25                  30

Phe Pro Tyr Ile Ala Ser Val Leu Thr Val Leu Phe Thr Leu His Lys
         35                  40                  45

Ala Ser Ile Pro Thr Met Lys Ile Ala Leu Arg Thr Ser Lys Cys Ser
     50                  55                  60

Tyr Lys Val Ile Lys Tyr Cys Ile Val Thr Ile Ile Asn Thr Leu Leu
 65                  70                  75                  80

Lys Leu Ala Gly Tyr Lys Glu Gln Val Thr Thr Lys Asp Glu Ile Glu
             85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
            115                 120                 125

Arg Ile His Asp Lys Leu Val Val Arg Pro Val Asp Ala Ile Asp Met
        130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175
```